(12) United States Patent
McErlean et al.

(10) Patent No.: US 12,174,242 B2
(45) Date of Patent: Dec. 24, 2024

(54) PORTABLE TEST APPARATUS AND METHOD OF TESTING RF/MICROWAVE TREATMENT SYSTEM

(71) Applicant: Emblation Limited, Alloa (GB)

(72) Inventors: Eamon McErlean, Alloa (GB); Gary Beale, Alloa (GB)

(73) Assignee: Emblation Limited, Alloa (GB)

( * ) Notice: Subject to any disclaimer, the term of this patent is extended or adjusted under 35 U.S.C. 154(b) by 112 days.

(21) Appl. No.: 17/626,937

(22) PCT Filed: Jul. 15, 2020

(86) PCT No.: PCT/EP2020/070038
§ 371 (c)(1),
(2) Date: Jan. 13, 2022

(87) PCT Pub. No.: WO2021/009253
PCT Pub. Date: Jan. 21, 2021

(65) Prior Publication Data
US 2022/0357391 A1 Nov. 10, 2022

(30) Foreign Application Priority Data

Jul. 15, 2019 (GB) .................................. 1910097
Jan. 31, 2020 (GB) .................................. 2001377

(51) Int. Cl.
*G01R 31/28* (2006.01)
*A61B 18/12* (2006.01)
(Continued)

(52) U.S. Cl.
CPC .......... *G01R 31/2822* (2013.01); *A61B 18/12* (2013.01); *A61B 18/1815* (2013.01);
(Continued)

(58) Field of Classification Search
USPC .................................. 324/637–646; 702/108
See application file for complete search history.

(56) References Cited

U.S. PATENT DOCUMENTS 4,292,960 A * 10/1981 Paglione .............. A61N 5/1016
607/156
6,428,356 B1 * 8/2002 Dole ....................... H01R 9/05
439/578
(Continued)

FOREIGN PATENT DOCUMENTS

CN 101578075 11/2009
TW 200949265 A 1/2009

OTHER PUBLICATIONS

Written Opinion issued in PCT/EP2020/070038 on Dec. 2, 2020.
(Continued)

*Primary Examiner* — Vincent Q Nguyen
(74) *Attorney, Agent, or Firm* — SNELL & WILMER L.L.P.

(57) ABSTRACT

A portable test apparatus for testing an RF/microwave treatment system may include a connector configured for connection to a generator or amplifier of the treatment system and/or to a distal end of a reusable transmission cable of the treatment system, a measurement device configured for measuring RF/microwave energy received through the connector and a test controller. The test controller may be configured to run at least one test of a set of tests for testing the treatment system, at least some of the set of tests comprising using the measurement device to measure RF/microwave energy supplied by a generator or amplifier of the treatment system to a proximal end of the reusable transmission cable and transmitted through the reusable transmission cable to the connector and analyse and/or record and/or output results of the set of tests.

13 Claims, 16 Drawing Sheets

(51) Int. Cl.
  *A61B 18/18* (2006.01)
  *A61B 90/00* (2016.01)
  *G01R 31/58* (2020.01)

(52) U.S. Cl.
  CPC .............. *A61B 90/08* (2016.02); *G01R 31/58* (2020.01); *A61B 2018/1823* (2013.01); *A61B 2090/0808* (2016.02)

(56) References Cited

U.S. PATENT DOCUMENTS

| | | |
|---|---|---|
| 8,242,782 B2 | 8/2012 | Brannan et al. |
| 9,192,425 B2 | 11/2015 | Behnke, II et al. |
| 9,861,424 B2 | 1/2018 | Behnke et al. |
| 2006/0142913 A1* | 6/2006 | Coffee .................. G01M 17/00 701/29.3 |
| 2006/0183995 A1 | 8/2006 | Bond et al. |
| 2008/0182524 A1 | 7/2008 | Graesslin et al. |
| 2010/0082025 A1 | 4/2010 | Brannan et al. |
| 2010/0144286 A1 | 6/2010 | Sorensen |
| 2011/0301905 A1 | 12/2011 | Gregg et al. |
| 2013/0257465 A1* | 10/2013 | Kassem .................. A61B 5/03 324/706 |
| 2014/0058697 A1* | 2/2014 | Zaostrovnykh ........ G01R 27/28 702/108 |
| 2014/0122009 A1 | 5/2014 | Meiyappan |
| 2015/0070029 A1* | 3/2015 | Libman .................. H05B 6/705 324/637 |
| 2017/0153283 A1 | 6/2017 | Gontier et al. |
| 2018/0214204 A1 | 8/2018 | Karmarkar |
| 2018/0313877 A1* | 11/2018 | Brant ..................... G01R 23/02 |
| 2019/0021792 A1 | 1/2019 | Brannan et al. |
| 2019/0090929 A1 | 3/2019 | Brannan |

OTHER PUBLICATIONS

The State Intellectual Property Office of People's Republic of China, Chinese First Office Opinion Notice dated May 25, 2024 in Application No. 202080064835.7.

EPO; European Office Action dated Jun. 11, 2024 in Application 20742691.7.

* cited by examiner

400 →
```
Bit/Signal
##/DUID measured
##/Reflected_Power_Test(1)
##/Generator_Green_Drive_Detected
##/HP_Button
##/Cable_Connected
##/Generator_Fusing_Current
##/HP_Green_Ring_Sensed
##/Handpiece_Connected
##/Reflected_Power_Test(0)
##/Tip_Connected
##/HP_Yellow_Ring_Sensed
##/Handpiece_Coax_Resistance_Sensed
##/Generator_Yellow_Drive_Detected
##/Generator_Fusing_Detection
##/No_MW_Power_Post_RP
##/Internal temperature (healthcheck)
##/Opt. External thermocouple temperature TC1/Trip
##/Opt. External thermocouple temperature TC2/Trip
##/Opt. Pump speed sensed
##/Opt. Acoustic signals sensed
```

Figure 12a

| 700 TEST | bit | 702 Website Description | 704 Logic 1 and calculation result message | 706 Logic 0 and calculation result message | 708 comment |
|---|---|---|---|---|---|
| Generator | | GENERATOR TEST STATUS | PASS | FAIL | Overall test outcome (if all pass then pass, if any fail then fail) |
| | N/A | Duty Cycle conversion from binary | PASS | FAIL | Sublevel message |
| | N/A | Output Power calculation | PASS | FAIL | Sublevel message (see generator power chart) |
| | ## | Generator_Green_Drive_Detected | PASS | FAIL | Sublevel message |
| | ## | Generator_Yellow_Drive_Detected | PASS | FAIL | Sublevel message |
| | ## | Generator_Fusing_Current | PASS | FAIL | Sublevel message |
| | ## | Generator_Fusing_Detection | PASS | FAIL | Sublevel message |
| | ## | Reflected_Power_Test(0) | PASS | FAIL | Sublevel message |
| | ## | Reflected_Power_Test(1) | PASS | FAIL | Sublevel message |
| | ## | No_MW_Power_Post_RP | PASS | FAIL | Sublevel message |

| | bit | 702 Website Description | 710 Calculation | 712 Lower limit | 714 upper limit | 716 Calculation note |
|---|---|---|---|---|---|---|
| Generator | | GENERATOR TEST STATUS | | | | |
| | N/A | Microwave Power output DC test | Duty cycle is calculated as a % in Binary (7 bits) | LOW % | HIGH % | |
| | N/A | Microwave Power output test | Output power = Power (W) * duty Cycle (%) | -## | +## | Power (W) is calculated by converting dBW to W i.e. P(W)=10^(P(dBW)/10) |
| | ## | Microwave GDD comms test | | | | |
| | ## | Microwave YDD comms test | | | | |
| | ## | Microwave FC comms test | | | | |
| | ## | Microwave FD comms test | | | | |
| | ## | Microwave Power reflected test (1) | | | | |
| | ## | Microwave Power reflected test (2) | | | | |
| | ## | Microwave Power reflected test (3) | | | | |

720

Generator Power Chart

| | | | | |
|---|---|---|---|---|
| | High | FAIL | FAIL | FAIL | >##% |
| DUTY CYCLE (%) | typical | PASS | PASS | FAIL | ##-##% |
| | very low | FAIL | FAIL | FAIL | <##% |
| | | low | typical | High | |
| | | <## W | ## - ## W | >## W | |
| | | | POWER (W) | | |

Figure 15

| | | 800<br>TEST | 802<br>Website Description | 804<br>Logic 1 and calculation result message | 806<br>Logic 0 and calculation result message | 808<br>DETAIL |
|---|---|---|---|---|---|---|
| | bit | N/A | N/A | PASS | FAIL | Overall test outcome (if all pass then pass, if any fail then fail) |
| Cable | | | CABLE TEST STATUS | | | |
| | ## | Cable_Connected | Cable comms test | PASS | FAIL | Sublevel message |
| | ## | Generator_Green_Drive_Detected | Microwave GDD comms test | PASS | FAIL | Sublevel message |
| | ## | Generator_Yellow_Drive_Detected | Microwave YDD comms test | PASS | FAIL | Sublevel message |
| | ## | Generator_Fusing_Current | Microwave FC comms test | PASS | FAIL | Sublevel message |
| | ## | Generator_Fusing_Detection | Microwave FD comms test | PASS | FAIL | Sublevel message |
| | N/A | Output Power calculation | Microwave Power output test | PASS | FAIL | Sublevel message (see cable power chart) |
| | ## | Reflected_Power_Test(0) | Microwave Power reflected test (1) | PASS | FAIL | Sublevel message |
| | ## | Reflected_Power_Test(1) | Microwave Power reflected test (2) | PASS | FAIL | Sublevel message |
| | ## | No_MW_Power_Post_RP | Microwave Power reflected test (3) | PASS | FAIL | Sublevel message |

| | | 802<br>Website Description | 810<br>Calculation | 812<br>Lower limit | 814<br>upper limit | 816<br>Calculation note |
|---|---|---|---|---|---|---|
| | bit | | | | | |
| Cable | N/A | CABLE TEST STATUS | | | | |
| | ## | Cable comms test | | | | |
| | ## | Microwave GDD comms test | | | | |
| | ## | Microwave YDD comms test | | | | |
| | ## | Microwave FC comms test | | | | |
| | ## | Microwave FD comms test | | | | |
| | N/A | Microwave Power output test | Output power = Power (W) * duty Cycle (%) | ## | ## | Power (W) is calculated by converting dBW to W i.e. P(W)=10^(P(dBW)/10) |
| | ## | Microwave Power reflected test (1) | | | | |
| | ## | Microwave Power reflected test (2) | | | | |
| | ## | Microwave Power reflected test (3) | | | | |

820

Cable Power Chart

| | | POWER (W) | | |
|---|---|---|---|---|
| | | low<br>< ## W | typical<br>## - ## W | High<br>> ## W |
| DUTY CYCLE (%) | High | FAIL | PASS | PASS | > ## % |
| | typical | FAIL | PASS | PASS | ##-## % |
| | very low | FAIL | FAIL | PASS | < ## % |

Figure 16

| | | | 900 | 902 | 904 | 906 | 908 |
|---|---|---|---|---|---|---|---|
| | | bit | TEST | Website Description | Logic 1 and calculation result message | Logic 0 and calculation result message | DETAIL |
| Handpiece | | N/A | N/A | HANDPIECE TEST STATUS | PASS | FAIL | Overall test outcome (if all pass then pass, if any fail then fail) |
| | | ## | Handpiece_Connected | Handpiece connection test | PASS | FAIL | Sublevel message |
| | | ## | Tip_Connected | Tip comms test | PASS | FAIL | Sublevel message |
| | | ## | HP_Button | Activation button test | PASS | FAIL | Sublevel message |
| | | ## | HP_Green_Ring_Sensed | GR comms test | PASS | FAIL | Sublevel message |
| | | ## | HP_Yellow_Ring_Sensed | YR comms test | PASS | FAIL | Sublevel message |
| | | ## | Handpiece_Coax_Resistence_Sensed | Microwave waveguide test | PASS | FAIL | Sublevel message |

Figure 17

PORTABLE TEST APPARATUS AND METHOD OF TESTING RF/MICROWAVE TREATMENT SYSTEM

CROSS-REFERENCE TO RELATED APPLICATIONS

This application is a national stage application of PCT/EP2020/070038, filed on Jul. 15, 2020, entitled "PORTABLE TEST APPARATUS AND METHOD OF TESTING RF/MICROWAVE TREATMENT SYSTEM," which claims priority to UK Application Nos. 1910097.3, filed on Jul. 15, 2019 and 2001377.7, filed on Jan. 31, 2020, all of which are hereby incorporated by reference in their entirety for all purposes.

FIELD

The present invention relates generally to a test apparatus and method for testing a treatment system, for example for a portable test apparatus for testing a microwave ablation system in the field.

BACKGROUND

It is known to provide a treatment system that is configured to perform RF or microwave heating and/or ablation of tissue. The treatment system may be referred to as a microwave ablation system or energy ablation system.

In most energy ablation systems the energy is delivered from an energy generator, via a connecting coaxial cable, to a radiating applicator that transfers the energy into the tissue. In these applicators, the radiating element may be surrounded by tissue, and may pierce tissue or be placed in contact with the tissue. For such systems, a typical standard practice is to deliver energy for a treatment lasting typically anywhere from 1 to 20 minutes, and specifically could also include any short duration such as 1 s, 2 s, 3 s, up to 5 s, or any time from 1 to 10 s up to 1 min. An objective of the energy delivery may be to raise the temperature of tissue greater than 43 to 45° C., greater than 60° C., greater than 70° C., greater than 100° C. or beyond such that tissue heating and/or necrosis or apoptosis occurs within the desired ablation zone. The energy may be delivered to have an amplitude or pulse width-modulated duty cycle to ensure that a specified level of energy is maintained or controlled for the duration of the energy release.

When performing high frequency electromagnetic energy delivery using coaxial cabling, energy may be lost within the cabling as heat along its length. Typically the cabling is designed to be practical and of sufficient length to ensure the specified energy is delivered to the treatment site. Interconnect coaxial cabling may be typically 1 to 2 meters in length, and for most applications this might be acceptable as the generator may be located close to the patient. The interconnecting coaxial cabling may be considered part of the treatment applicator/antenna and may therefore be considered to be disposable. The interconnecting coaxial cabling may be a reusable cable that connects to the treatment applicator/antenna.

In some circumstances, high frequency coaxial cabling may have the possibility to be easily damaged by being crushed or kinked which may cause reflection or absorption of energy.

This can complicate the delivery of energy to the treatment applicator. Typically the energy generator system may measure applied power and reflected power. Typically the applied microwave power may be required to be within +/−20% of the set (or expected) power in Watts or relative units according to the 60601-2-6 standard. The power delivered via the cable may be 70-90% of the power supplied by the generator due to cable loss. This loss typically depends upon cable construction, cable materials, dimensions, frequency of use and may typically be 70-80% of the power supplied by the generator at 8 GHz. However in the case of a damaged reusable cable that is absorbing energy, the applied power may be determined by the system as being within specification as the energy is being accepted by the absorbing cabling, even though the energy is not being received by the applicator. Likewise the reflected power may also be measured as minimal due to the energy being absorbed at a point along the cable. Absorption of energy by a damaged cable may result in excessive cable heating and under-treatment. A user may have no immediate means to identify that the system is not operating sufficiently and delivering the required energy to the target location under this condition.

Typically, the treatment system component parts are inspected and tested during manufacture and periodically at defined service intervals, which may be in yearly multiples. This could mean in the event of damage that a particular system may operate for some time before such damage is identified.

Typically, the generator is configured to trip (for example, to cease operation) when reflected power is too high, for example if the reflected power is higher than a threshold value. A reflected power trip test may be performed to determine whether the generator trips as expected. The reflected power trip test is particularly important as it utilises the loss property of cable twice (forward and back) in conjunction with the power supplied by the generator. If the cable is damaged or the machine is out of specification this test will quickly fail and thus can uniquely identify faults at the system level.

SUMMARY

In a first aspect, there is provided a portable test apparatus for testing an RF/microwave treatment system, the portable test apparatus comprising: a connector configured for connection to a generator or amplifier of the treatment system and/or to a distal end of a reusable transmission cable of the treatment system; a measurement device configured for measuring RF/microwave energy received through the connector; and a test controller configured to: run at least one set of a set of tests for testing the treatment system, at least some of the set of tests comprising using the measurement device to measure RF/microwave energy supplied by a generator or amplifier of the treatment system to a proximal end of the reusable transmission cable and transmitted through the reusable transmission cable to the connector; and analyse and/or record and/or output results of the set of tests.

The connector, the measurement device and the test controller may be housed in a single housing.

The analysing of the results by the test controller may comprise comparing the measured RF/microwave energy to predicted RF/microwave energy.

The analysing of the results by the test controller may comprise comparing a measured value for a RF/microwave energy parameter to a threshold value for the RF/microwave energy parameter.

The RF/microwave energy parameter may comprise at least one of a voltage, a current, a power.

The analysing of the results by the test controller may comprise comparing a measured profile of the RF/microwave energy to an expected profile.

The analysing of the results by the test controller may comprise determining whether the reusable transmission cable is damaged and/or absorbing. The determining may be based on the comparing of the measured RF/microwave energy to predicted RF/microwave energy.

The analysing of the results by the test controller may comprise calculating a delivered power value using a measured power value and duty cycle value. The outputting of the results may comprise outputting the delivered power value without the measured power value and duty cycle value. The outputting of the results may comprise outputting the delivered power value, measured power value and duty cycle value.

The apparatus may further comprise a first transmission path configured to transmit RF/microwave energy from the connector to the measurement device, and at least one further transmission path configured to transmit RF/microwave energy from the connector to at least one further RF/microwave component.

The apparatus may further comprise a switch configured to switch between the first transmission path and the at least one further transmission path, wherein the switching of the switch is controlled by the test controller. The test controller may be configured to control the switch to switch between the first transmission path and the at least one further transmission path to perform different tests of the set of tests. Each test of the set of tests may comprise directing RF/microwave energy from the connector to a respective one of the first transmission path and the at least one further transmission path. The at least one further transmission path may comprise multiple further transmission paths. The switch may be configured to switch between the multiple further transmission paths.

The switch may be housed in the housing. The first transmission path may be housed in the housing. The at least one further transmission path may be housed in the housing. The at least one further RF/microwave component may be housed in the housing.

The at least one RF/microwave component may comprise at least one reflecting component configured to reflect at least part of the RF/microwave energy back along the further transmission path through which it was transmitted to the at least one reflecting component.

The at least one reflecting component may comprise at least one mismatch.

The at least one reflecting component may comprise a plurality of reflecting components, each associated with a respective further transmission path. Each reflecting component may provide a known degree of reflection. Each reflecting component may provide a known mismatch. The switch may be configured to switch between the further transmission paths, thereby providing different reflections.

The at least one RF/microwave component may comprise at least one RF/microwave load.

The at least one RF/microwave component may comprise a plurality of RF/microwave loads, each associated with a respective further transmission path. The switch may be configured to switch between the further transmission paths, thereby sending RF/microwave energy to each of the plurality of microwave loads. The test controller may be configured to control the switch to switch between the further transmission paths.

The at least one RF/microwave component may comprise an open circuit. The at least one RF/microwave component may comprise a short circuit.

The at least one further transmission path may comprise a plurality of transmission paths having different transmission path lengths.

The at least one RF/microwave component may be configured to simulate at least one system condition. The test controller may be configured to determine whether the generator or amplifier responded as expected to the simulated at least one system condition.

The system condition may comprise a system fault. The system condition may comprise a short circuit. The system condition may comprise an open circuit. The system condition may comprise a condition of the reusable cable. The system condition may comprise damage to the reusable cable. The system condition may comprise losses in the reusable cable. The system condition may comprise a condition of an RF/microwave applicator device of the system. The system condition may comprise an identity.

The at least one test of the set of tests may comprise sending at least one signal from the portable test apparatus to the generator or amplifier.

The at least one test of the set of tests may comprise verifying a response of the generator or amplifier to the at least one signal.

The at least one test of the set of tests may further comprise at least one data communication test. The at least one data communication test may comprise testing data communication to the generator or amplifier. The at least one data communication test may comprise testing data communication from the generator or amplifier.

The set of tests may be configured to test a plurality of parameters associated with the treatment system, the parameters including at least some of: continuity, voltage, current, resistance, electromagnetic energy, signal timing, identity, an audible alert, a visual alert, a visible indicator.

The at least one test of the set of tests may comprise measuring resistance properties and/or pulse/transient distance to fault timings to determine the integrity of at least one coaxial pathway.

The apparatus may further comprise a temperature measurement device. The test controller may be configured to receive a temperature measurement from the temperature measurement device. The test controller may be configured to adjust a result of the at least one test in dependence on the temperature measurement device. The temperature measurement device may be housed in the housing. The temperature measurement device may be positioned in proximity to the measurement device.

The apparatus may further comprise a memory configured to store the set of tests, wherein the test controller is configured to select the at least one test from the memory.

The running of the at least one test of the set of tests may be automated.

The apparatus may further comprise a communication means configured to instruct the generator or amplifier to output energy. The communication means may be configured to instruct the generator or amplifier to output energy in accordance with at least some of the set of tests. The communication means may be configured to instruct the generator or amplifier to output energy in accordance with the least one test of the set of tests. The communication means may be housed in the housing.

The apparatus may further comprise a further connector configured to connect to an RF/microwave applicator device. The at least one test of the set of tests may further comprise at least one test for testing the RF/microwave applicator device.

The testing of the RF/microwave applicator device may comprise testing a functionality of the RF/microwave applicator device. The testing of the RF/microwave applicator device may comprise testing an electrical property of the RF/microwave applicator device. The testing of the RF/microwave applicator device may comprise testing an identity of the RF/microwave applicator device. The testing of the RF/microwave applicator device may comprise testing usage status of the RF/microwave applicator device. The testing of the RF/microwave applicator device may comprise testing communication to the RF/microwave applicator device.

The least one test of the set of tests may comprise sending at least one signal from the portable test apparatus to the RF/microwave applicator device. The at least one test of the set of tests may comprise verifying a response of the RF/microwave applicator device to the at least one signal.

The set of tests may comprise a reflected power trip test. The reflected power trip test may comprise determining by the test controller whether the generator or amplifier trips when RF/microwave energy is directed to the at least one reflecting component. The reflected power trip test may comprise controlling the switch to direct RF/microwave energy from the controller: to the measurement device via the first transmission path during a first time period; to the at least one reflecting component via at least one further transmission path during a second, subsequent time period; and to the measurement device via the first transmission path during a third, subsequent time period.

The reflected power trip test may comprise, if RF/microwave energy received by the measurement device during the third period exceeds a threshold value, determining by the test controller that the generator or amplifier did not trip when the energy was directed to the at least one reflecting component.

The apparatus may further comprise a display configured to display a representation of at least one result of the set of tests. The display may be housed in the housing.

The at least one result may be encoded as at least one code word. Each code word may be unique. The at least one code word may comprise at least one binary word and/or at least one hexadecimal word and/or at least one multi-letter language word.

The test apparatus may be configured to output at least one result of the set of tests to at least one further device. The test apparatus may be configured to output at least one result of the set of tests to a website. The test apparatus may be configured to output at least one result of the set of tests to a database.

The outputting may comprise encoding the at least one result as at least one code word, and outputting the at least one code word.

The apparatus may be further configured to adjust settings of at least part of the treatment system. The apparatus may be further configured to reprogram at least part of the treatment system.

The RF/microwave treatment system may comprise a microwave ablation system.

The RF/microwave applicator device may comprise a microwave ablation applicator device.

The RF/microwave applicator device may be configured to provide microwave ablation.

The RF/microwave applicator device may be configured to provide tissue heating.

The RF/microwave applicator device may be configured to provide coagulation.

The RF/microwave applicator device may be configured to provide hyperthermia.

The RF/microwave applicator device may be configured to provide RF treatment.

The RF/microwave applicator device may be configured to provide microwave treatment.

In a further aspect, there is provided a test method for testing an RF/microwave treatment system using a portable test apparatus, the test method comprising: connecting a generator or amplifier of the treatment system to a connector of the portable test apparatus and/or connecting a distal end of a reusable transmission cable of the treatment system to a connector of the portable test apparatus; running, by a test controller of the portable test apparatus, at least one test of a set of tests for testing the treatment system, at least some of the set of tests comprising using the measurement device to measure RF/microwave energy supplied by a generator or amplifier of the treatment system to a proximal end of the reusable transmission cable and transmitted through the reusable transmission cable to the connector; and, by the test controller, analysing and/or recording and/or outputting results of the set of tests.

The test method may further comprise connecting a RF/microwave applicator device of the treatment system to a further connector of the portable test apparatus. The set of tests may include at least one RF/microwave applicator test.

The outputting of results of the set of tests may comprise outputting at least one code word.

The test method may further comprise analysing the at least one code word. The analysis may comprise a check of validity of the code word. The analysis may comprise a check of integrity of the code word. The analysis may comprise determining a proof of a test being run. The analysis may comprise deciphering the test results. The analysis may comprise interpreting the test results.

The test method may further comprise outputting an instruction to an operator in dependence on the test results. The instruction may comprise instructions to remedy a failure, to repeat at least one test of the set of tests, or to perform at least one further test.

In a further aspect of the invention, which may be provided independently, there is provided a reflected power trip test method comprising determining by the test controller whether the generator or amplifier trips when RF/microwave energy is directed to the at least one reflecting component, the reflected power trip test comprising controlling the switch to direct RF/microwave energy from the controller: to the measurement device via the first transmission path during a first time period; to the at least one reflecting component via at least one further transmission path during a second, subsequent time period; and to the measurement device via the first transmission path during a third, subsequent time period. The reflected power trip test may comprise, if RF/microwave energy received by the measurement device during the third period exceeds a threshold value, determining by the test controller that the generator or amplifier did not trip when the energy was directed to the at least one reflecting component.

In a further aspect, which may be provided independently, there is provided a reflected power trip test method comprising: connecting a device under test to a connector of a test apparatus; measuring, by a measurement device of the test apparatus, RF/microwave energy supplied by the device under test to the connector during a first time period; adjusting a setting of the test apparatus such that RF/microwave energy received at the connector is directed to a mismatch instead of to the measurement device during a second time period; adjusting the setting of the apparatus such that RF/microwave energy received at the connector is again directed to the measurement device during a third period; and if RF/microwave energy received by the measurement device during the third period exceeds a threshold value, determining that the generator or amplifier did not trip when the energy was directed to the mismatch.

Test hardware may be provided which is used to check energy and data communication to and from an applicator/antenna in a medical energy system used to deliver energy into biological tissues for ablative or non-ablative purposes.

A means to verify performance of a RF/Microwave medical system may be provided. The method may include a test device or system, electromagnetic energy generator/amplifier system, cabling and applicator used to deliver energy from a generator/amplifier system to a recipient device, for example a radiating applicator or antenna that transfers the energy into biological tissue for treatment purposes (which may collectively be called a treatment system or RF/Microwave treatment system).

Energy and signals/data may be delivered from the treatment system into a test device. The test device may be used to confirm correct operation and/or to determine performance or usage parameters of the RF/Microwave system, in particular energy delivery.

A portable test device may be provided for use with electromagnetic ablation equipment. This test may be carried out in-field as well as at regional service centres. Due to the intuitive test setup it may be carried out by any trained person and not just specialist service technicians.

The portable test device or system may determine if an adequate level of energy is being delivered to the treatment applicator from the reusable components of a medical RF/Microwave treatment system. Various conditions such as high reflected power or other system properties such as identity or other aspects of use may also be simulated, to ensure the overall performance of the system is as expected. The simulation of such conditions may also be used for training purposes to simulate the expected outcome of specific variations in operation that a user may expect. Current performance may be compared to historical performance to determine changes in device performance over time.

The test apparatus may accommodate these activities to determine the fitness of the treatment equipment for use or to determine if the unit needs to be returned to the service centre for a more detailed analysis. The test apparatus may also record or report or communicate usage data or other information to facilitate record keeping, analysis, and costs relating to the inspection activity.

The test apparatus may allow the treatment system performance to be tested more regularly or prior to use, to ensure the equipment is operating as expected. To utilise engineering test-bench equipment used in manufacture may not be practical in the field due to cost, training and logistical complexities. A portable device may be provided that is configured to verify the fitness of the treatment system for use.

In a further aspect, which may be provided independently, there is provided a computing apparatus comprising processing circuitry configured to: receive at least one code word, the at least one code word encoding results for a set of tests performed on at least part of an RF/microwave treatment system using a portable test apparatus; decode the at least one code word to obtain the results for the set of tests; analyse the results to obtain a pass or fail value for at least one of: the RF/microwave treatment system, a generator or amplifier of the RF/microwave treatment system, a reusable transmission cable of the RF/microwave treatment system, a handpiece of the RF/microwave treatment system, an applicator tip of the RF/microwave system; and display the pass or fail value to a user.

The receiving of the at least one code word may comprise receiving an input provided by the user via a website. The processing circuitry may be configured to display the pass or fail value to the user via the website.

The decoding of the at least one code word may comprises extracting a measured power value from a first part of the at least one code word and extracting a duty cycle value from a second, different part of the at least one code word. The analysing of the results may comprise calculating a delivered power value using the measured power value and duty cycle value.

The processing circuitry may be configured to display the delivered power value to the user. The processing circuitry may be configured to display the delivered power value to the user without displaying the measured power value or duty cycle value.

The decoding of the at least one code word may comprise extracting a delivered power value from the at least one code word. The decoding of the at least one code word may further comprise extracting a measured power value and a duty cycle power value from the at least one code word.

The results of the set of tests may comprise numerical results for one or more test parameters. The pass or fail result may be displayed to the user without the numerical results of the set of tests being displayed to the user.

The computing apparatus may further comprise a data store configured to store the at least one code word. The data store may be further configured to store the numerical results of the set of tests.

The processing circuitry may be configured to analyse the numerical results of the set of tests for engineering and/or quality assurance.

The analysing of the results may comprise comparing measured RF/microwave energy to predicted RF/microwave energy. The analysing of the results may comprise comparing a measured value for a RF/microwave energy parameter to a threshold value for the RF/microwave energy parameter. The analysing of the results may comprise comparing a measured profile of the RF/microwave energy to an expected profile. The analysing of the results may comprise determining whether the reusable transmission cable is damaged and/or absorbing.

In a further aspect, which may be provided independently, there is provided a method comprising: receiving at least one code word, the at least one code word encoding results for a set of tests performed on at least part of an RF/microwave treatment system using a portable test apparatus; decoding the at least one code word to obtain the results for the set of tests; analysing the results to obtain a pass or fail value for at least one of: the RF/microwave treatment system, a generator or amplifier of the RF/microwave treatment system, a reusable transmission cable of the RF/microwave treatment system, an applicator and/or applicator handpiece and/or applicator tip of the RF/microwave system; and displaying the pass or fail value to a user.

There may be provided a method or system substantially as described herein with reference to the accompanying drawings.

Features in one aspect may be provided as features in any other aspect as appropriate. For example, features of a method may be provided as features of an apparatus and vice versa. Any feature or features in one aspect may be provided in combination with any suitable feature or features in any other aspect.

BRIEF DESCRIPTION OF THE DRAWINGS

Embodiments of the invention are now described, by way of non-limiting example, and are illustrated in the following figures, in which:

FIG. 12a is a list of results encoded in a code word;

FIG. 15 is a table of generator tests and outcomes;

FIG. 16 is a table of cable tests and outcomes; and

FIG. 17 is a table of handpiece tests and outcomes.

DETAILED DESCRIPTION

Figure 1:
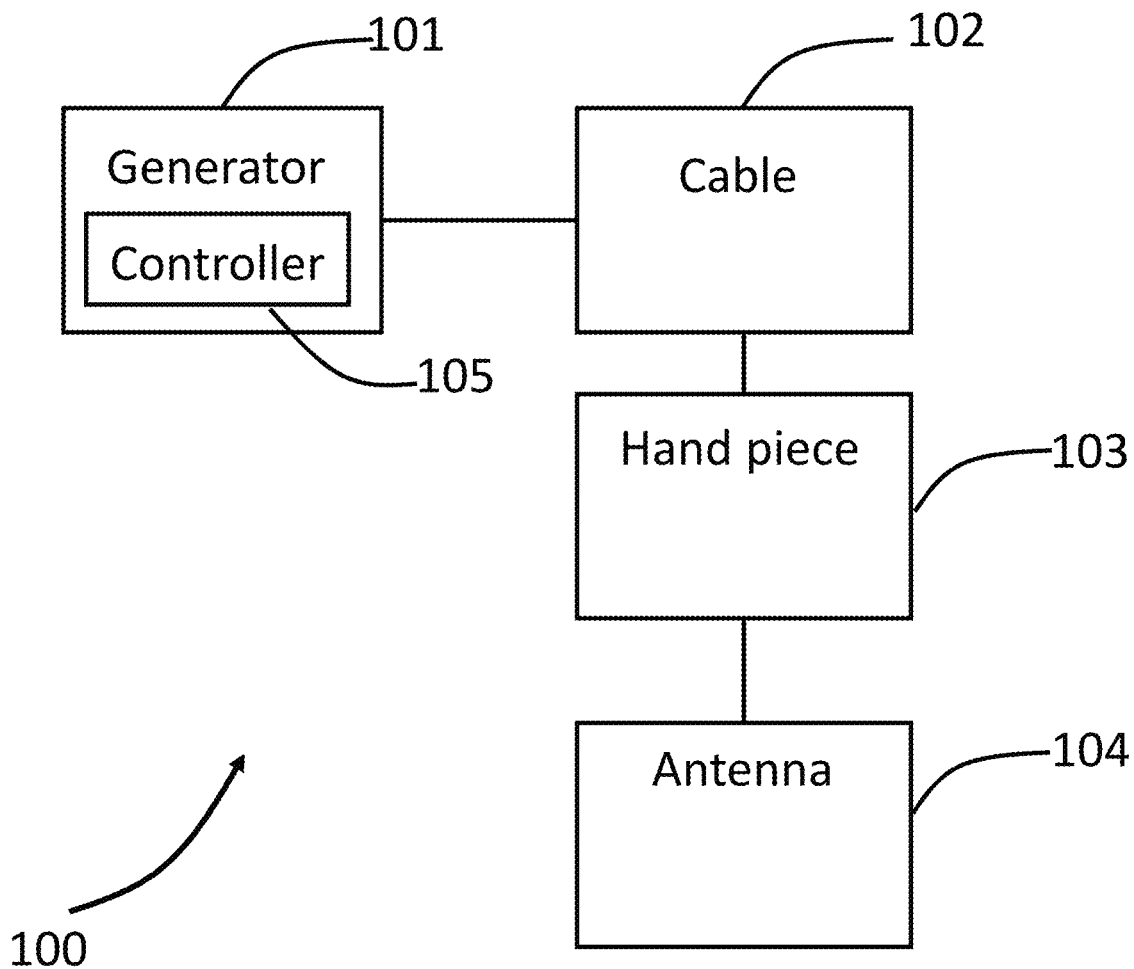
FIG. 1 is a schematic illustration of an example of a treatment system.

FIG. 1 illustrates an example of a microwave treatment system generally designated 100 for treating a tissue. The microwave system 100 comprises a microwave generator 101 for providing microwave energy, a flexible interconnecting microwave cable such as a coaxial cable 102, a hand grip or hand piece 103, and a microwave antenna apparatus 104. The antenna apparatus 104 may also be referred to as an applicator or radiating applicator or applicator tip. The microwave generator 101 comprises a controller 105 configured to select a frequency of microwave energy provided to the cable apparatus and/or a power of microwave energy provided to the cable apparatus.

In use, the controller 105 selects an operational frequency or range of frequencies and controls the microwave generator 101 to provide microwave energy at the operational frequency or range of frequencies to the microwave cable 102. The microwave cable 102 provides microwave energy to the antenna apparatus 104. The antenna apparatus 104 is positioned in or adjacent to tissue, for example tissue of a human patient or other subject. The antenna apparatus 114 radiates microwave energy into the tissue, causing tissue heating. The tissue heating may be such as to cause ablation, coagulation, hyperthermia or treatment.

Figure 2:
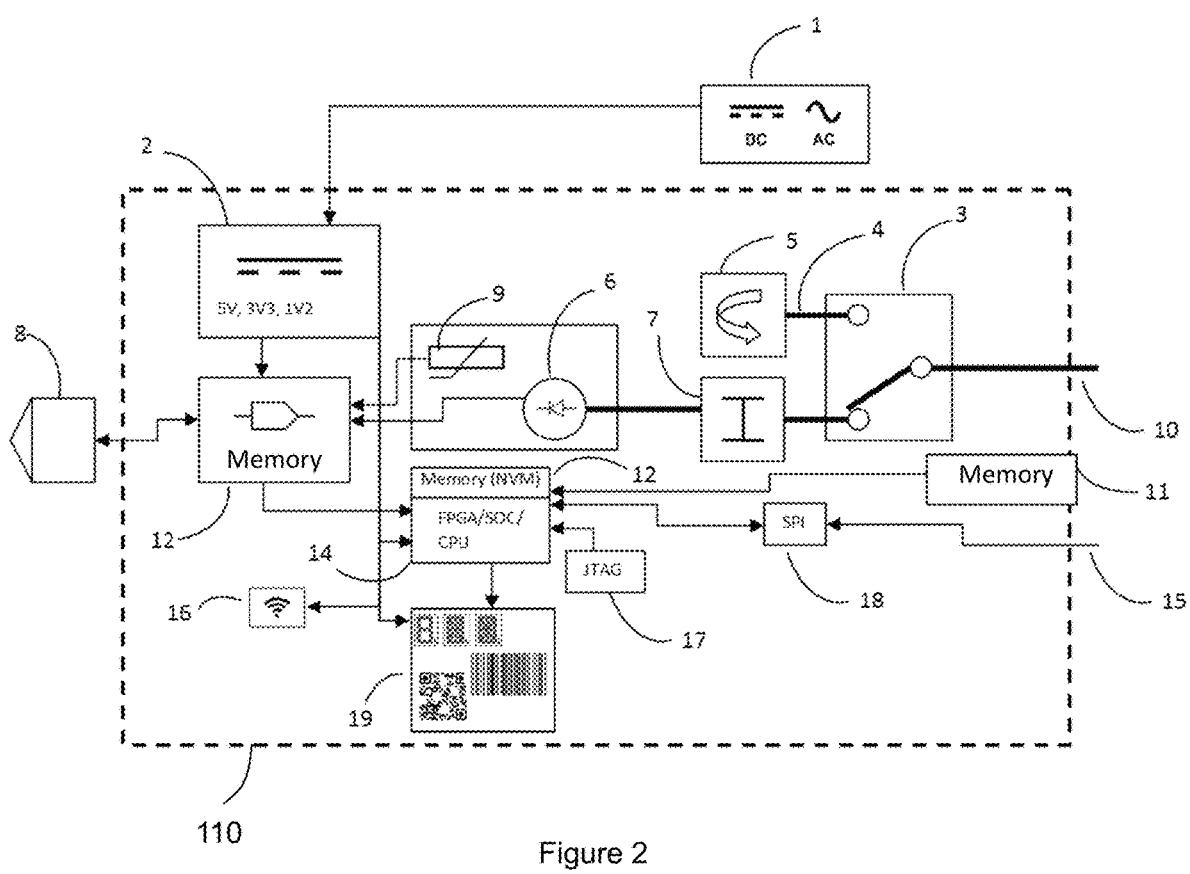
FIG. 2 is a schematic illustration of a portable test device for use with a RF/Microwave ablation system.

A schematic representation of a portable test device (tester) 110 in accordance with an embodiment is illustrated in FIG. 2. The portable test device 110 is configured to test the coaxial cable 102 when coupled to the microwave generator 101. In the present embodiment, the portable test device 110 is also configured to test the antenna apparatus or applicator 104, which is shown in FIG. 2 as applicator 8. In further embodiments, the portable test device 110 may be configured to test the applicator 104 when it is not in combination with the microwave generator 101.

In FIG. 2 an AC to DC power supply adapter 1 powers the test unit 110. In other embodiment, power may also or alternatively be delivered by an embedded battery, for example a lithium-ion or lithium polymer rechargeable battery (not shown). The DC power may be subdivided into a number of internal power supplies 2, which may power various components or circuits within the tester 110.

In the embodiment of FIG. 2, the tester 110 is configured to be coupled to the distal end of the coaxial cable 102, which is the end of the coaxial cable to which an applicator 104 would usually be attached in use. The tester 110 is configured to receive electromagnetic energy 10 from the microwave generator 101 via the coaxial cable 102.

The electromagnetic energy 10 may be delivered to an internal microwave switch 3. Energy may then be delivered from the switch via a physical length of transmission line possessing a fixed electrical phase length of between 0 or 360 degrees or a multiple of 180 degrees such as 540 or 720 degrees. The transmission line 4 may either direct the energy to a mismatch 5 (short or open circuit or other impedance mismatch) or to a detector 6 (diode detector, mixer detector or thermister power sensor) via an attenuator 7. The microwave switch 3 may possess multiple switch pathways. The microwave switch 3 may switch between a plurality of known mismatches and/or reflections (open and short circuit) and/or may switch between identical fixed impedances and/or mismatches and reflections (open and short circuit) across multiple electrical paths with a plurality of electrical phase lengths to fully test the reflected power performance of the device under test. The portable test device 110 may also cause or command the device under test (in this case, microwave generator 101) to output a fixed frequency or output a plurality of frequencies across a specified bandwidth, either discretely, individually, in order or varied continuously. For example, the portable test device 110 may instruct the device under test 101 to output frequencies across or within the FCC ISM band 2.4 GHz to 2.5 GHz or any range within or other ranges or ISM bands or any range subset from 1 to 100 GHz, for example 7 to 9 GHz, 7.5 to 8.5 GHz, 7.95 to 8.05 GHz.

The detector 6 detects power that is transmitted by the microwave generator 101 and transmitted via the coaxial cable 102 to the portable test device 110. The detected power may be measured as a peak or maximum or average or RMS level or logarithmic level. The detected power may be sampled by an analogue to digital converter (ADC) 13. The ADC 13 may communicate with a field programmable gate array (FPGA) or system on a chip (SOC) or embedded hardware or software CPU 14. The FPGA or SOC or CPU 14 may measure and analyse the result against a calibrated target. The FPGA or SOC or CPU 14 may present the data to the user via a display 19, which may be displayed on a display component, for example a display area 20 as described below with reference to FIG. 3.

The FPGA or SOC or CPU 14 may also act as a test controller. The test controller may be configured to select at least one test procedure to be performed by the portable test device 110. The test controller may control the portable test device 110 to perform the selected at least one test procedure. The test controller may control the microwave generator 101 to provide microwave energy in accordance with the selected at least one test procedure. In other embodiments, the function of the test controller may be provided by a different component of the portable test device 110, which may be a component that is not shown in FIG. 2.

The measurements obtained by the portable test device 110 may also include a temperature input 9 from the detector 6 that is being sampled by ADC 13. The temperature measurement may be used to improve the measurement accuracy by compensating for changes in the ambient and in-circuit temperature.

The tester 110 may also incorporate a SPI communication bus 15 and SPI controller 18 for communications within the device or outside the device to external peripherals. In other embodiments, any suitable communications means may be used.

The FPGA/SOC/CPU 14 may have a local interface 17 (for example an interface in accordance with Joint Test Action Group, JTAG, standards or similar) to be used to program and externally calibrate the portable test device. The calibration and look-up information may be stored for reference in non-volatile memory 12 in the FPGA/SOC/CPU 14 or on local solid state memory 11 within or connectable to the tester 110 via a memory slot (not shown).

The memory 11, or any suitable memory, may be used to store a set of tests from which the test controller selects one or more tests to be performed as part of a given test procedure.

The portable test device 110 via the ADC 13 may also test communication to the applicator/antenna 8. The portable test device 110 may interrogate identity, usage status, communication, and/or functionality (lamps, switches) of the applicator 8. The portable test device 110 may measure resistance properties or pulse/transient distance to fault (DTF) timings to determine the integrity of coaxial pathways. The portable test device 110 may also be capable of programming or modifying the antenna identity or treatment characteristics, such as lifetime, reuse, or performance for special purposes such as demonstrations etc.

Figure 3:
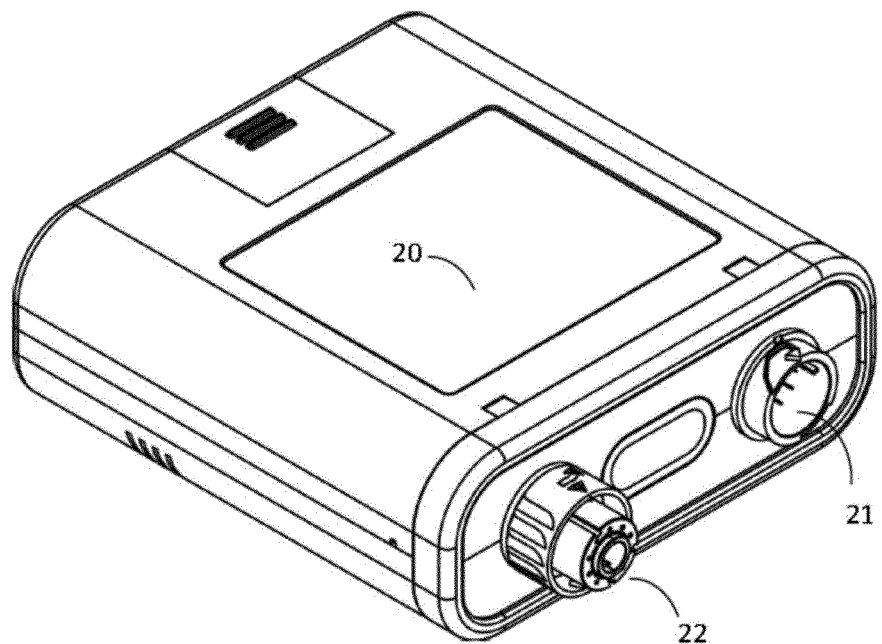
FIG. 3 is an outline diagrammatic illustration of a portable test device for use with a RF/Microwave ablation system.

FIG. 3 shows a front view of the portable test device 110 in accordance with the present embodiment. The portable test device 110 may comprise an enclosure as illustrated in FIG. 3 that houses all the components and PCB assemblies.

The portable test device 110 may possess two connections, a first connection 21 for connection of the energy delivery cable 102 and a second connection 22 for connection of the applicator/antenna 8. These connections 21, 22 in the present embodiment are based upon Amphenol Pulse-Lok PL1200 connectors and incorporate signal and data lines in addition to coaxial microwave BMA connectors. These coaxial connectors 21, 22 may be any common coaxial connector type such as SMA, N-Type, BNC, SMP, APC, 7 mm, K, etc.

A display area 20 may report test data including codes or other information to be recorded or conveyed. This code may be reported as a hexadecimal word, for example 64 bit, 16 characters A-F 0-9, or may be reported as a series of multi-letter language words, for example six combinations of 4 letter words=6(5454 words in English) or five 5 letter words=5(12478 words in English). Other combinations may be chosen with sufficient redundancy to cover the numerical problem space (for example, 50 to 64 bits depending upon test redundancies). A list of words may be used which may comprise any character based word list from any language. The word list(s) may be stored within the product in non-volatile RAM with each word having a unique indexer or reference in the list corresponding to a binary or hexadecimal equivalent word.

In the present embodiment, the display area 20 outputs a 64 bit word as a 16 digit HEX code that reports results including but not limited to the following data including checksum bits used to hash the overall word to prevent casual interpretation or deliberate code construction:

| | |
|---|---|
| Unit Serial Number | Number (tester) |
| Tests Remaining | (Number/1000) (service interval for the tester) |
| Temperature | Number/Degrees |
| Microwave Average Power | result + raw data (P_Ave) |
| Microwave Peak Power | result + raw data (P_Pk) |
| Microwave Duty cycle | result + raw data (P_Dty) |
| Coax Resistance | result + raw data (resistance Ω) |
| Reflected Power Test | Pass/fail |
| Generator Fuse Current | Pass/fail |
| Generator Yellow LED | Pass/fail |
| Generator Green LED | Pass/fail |
| Handpiece Yellow LED | Pass/fail |
| Handpiece Green LED | Pass/fail |
| Handpiece Button | Pass/fail |

Due to the variations and permutations in the bits required to construct the 16 digit HEX code, the same code cannot be repeated therefore all new codes can be compared to all used codes to prevent code reuse for security reasons.

In other embodiments, other information may be communicated. The HEX word may be longer or shorter than the HEX word described above.

The data may be securely stored on local solid state memory 11 within or connectable to the tester 110 via a memory slot (not shown). This may include a means of encryption to prevent unauthorised reading by third parties. In other embodiments, any suitable memory may be used to store test results.

Figure 4:
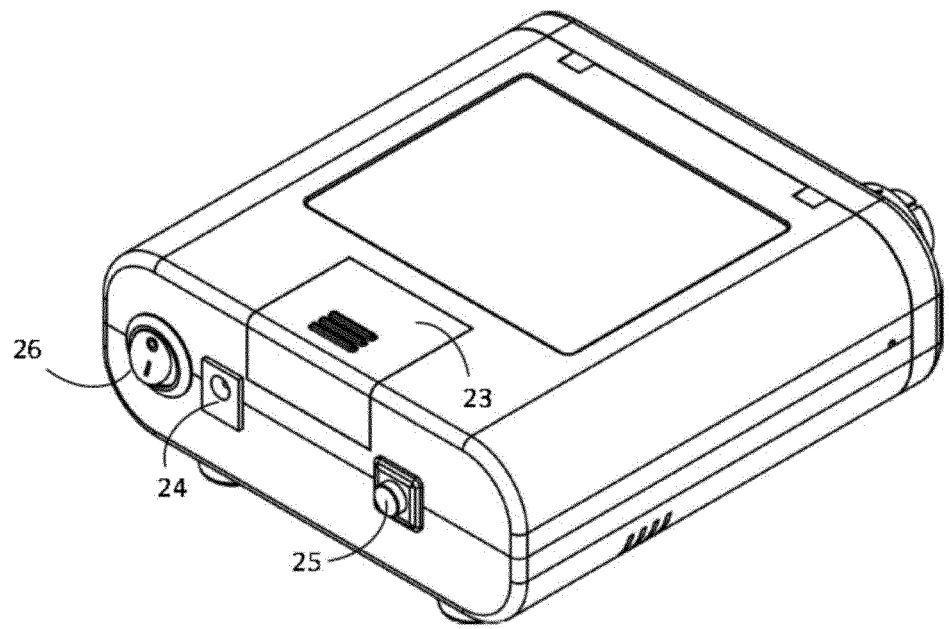
FIG. 4 is an outline diagrammatic illustration of a portable test device for use with a RF/Microwave ablation system.

FIG. 4 shows a rear view of the portable test device 110 in accordance with the present embodiment. As illustrated in FIG. 4 the portable test device may have an isolating power switch 26, DC input jack 24, test or rest button 25 and storage compartment 23 for test accessories or to store rechargeable batteries depending upon configuration.

This display 20 may be simple LCD, LED, OLED, alphanumeric, dot-matrix or any suitable display format. The display 20 may also display a 1D or 2D barcode that may be readable to contain a summary of the test results or coded data. The summary may comprise information including but not limited to measured power, delivered power, fusing performance, temperature, time, date, test duration, serial number of test device, serial number relating to the device(s) under test (DUTs), fault codes, usage count, test limits, pass/fail criteria, calibration date of portable tester, calibration date of DUTs, employee ID, service date, previous test information, any other relevant status or detail. In other embodiments, the summary may be provided using any suitable display method. The summary may be output by any suitable method, which in some embodiments may not comprise displaying the summary. The summary may be exported to any suitable device.

This displayed information or codes may be optically captured by a camera (not shown) used by a mobile hardware application (app) running on a tablet, phone or PC (not shown) to scan or photograph the portable tester display 110 and then interpret this information and store or communicate the data to a centralised database. The data may also include photos, audio or video of the service event or recordings of performance or other notes written or spoken or otherwise recorded by the test personnel.

The mobile hardware application may be able to read the local solid state memory 11 within or connectable into the tester 110 via the memory slot. The local solid state memory 11 in the portable tester 110 may be removable to be read by an adapter (not shown) in the mobile hardware using a secure software application and appropriate decryption to open the data. The memory 11 may be used to store the data for each service episode for the test equipment to provide a record of the service life of the portable test device.

The mobile hardware application may also be able to communicate directly to the tester 110 via the SPI bus 15 using an SPI adapter with the mobile hardware universal serial port (USB). The portable test device 110 may also communicate physically via SPI and/or USB with external peripherals, networks, and computers or with the medical system under test to store or communicate the data to a database or network location.

The portable test device 110 may also communicate wirelessly via a wireless transceiver 16. The portable test device 110 may communicate wirelessly with external peripherals, networks, computers, phones, tablets, Smartphone, or smartwatch devices or with the medical system or accessories under test using any suitable form of wireless communication, for example Bluetooth®, WIFI™, Zigbee®, or WIMAX®. The portable test device 110 may also communicate wirelessly with mobile networks such as GSM™, UMTS, CDMA2000, LTE, 3G, 4G, or 5G. The portable test device 110 may use a subscriber identification module identity (SIM) (not shown) to store or communicate the data to a database or network location. The portable test device 110 may be able to communicate wirelessly using high frequency audio/ultrasound to communicate with smartphone, smartwatch or tablet devices, for example using audio frequency modulation or via the SilverPush Software Development Kit (SDK).

The data stored may be used to monitor servicing, monitor calibration, trend performance, gather usage information, plan maintenance and/or determine financial invoicing for services provided. The data stored may be used to extract metrics around the performance of the service or equipment as required.

The portable test device 110 may be able to determine the continuity or integrity of conductive connections for the reusable cable 102. The portable test device 110 may be able to determine the continuity or integrity of conductive connections for the antenna or applicator 8.

The portable test device 110 may be able to trigger and sense the delivery of microwave power. The portable test device 110 may be able to act as a good microwave load. The portable test device 110 may be able to simulate a fault condition such as a mismatch to ensure the electromagnetic energy generator/amplifier system 101 functions correctly in those conditions.

Figure 5:
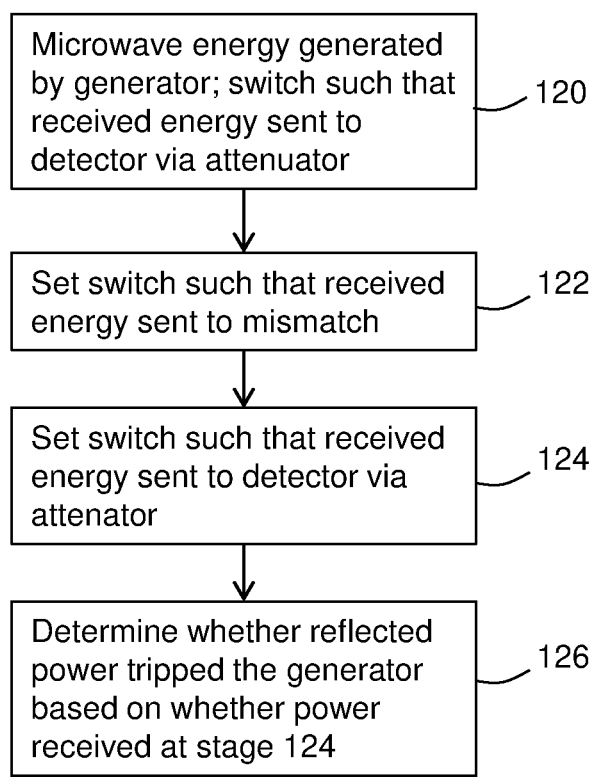
FIG. 5 is a flow chart illustrating in overview a reflected power trip test in accordance with an embodiment.
Figure 6:
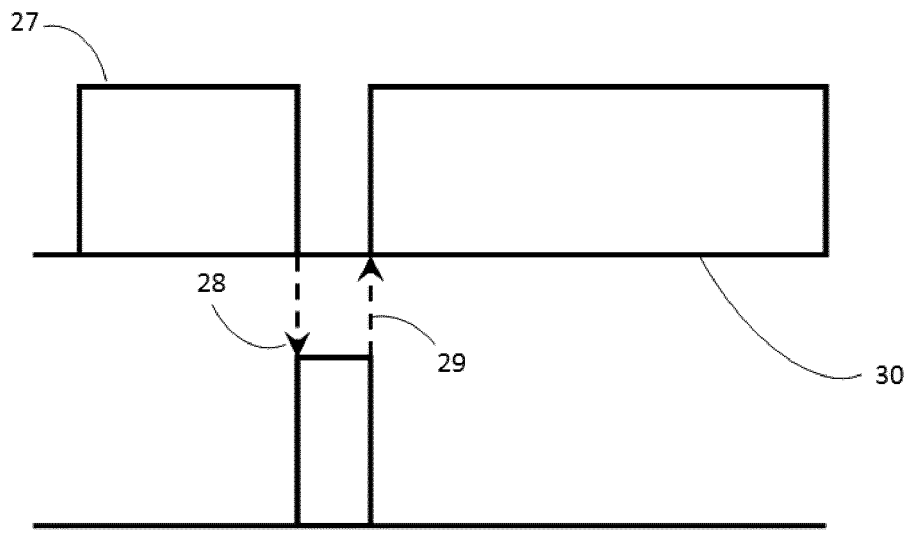
FIG. 6 and FIG. 7 are diagrammatic illustrations of a test sequence.
Figure 7:
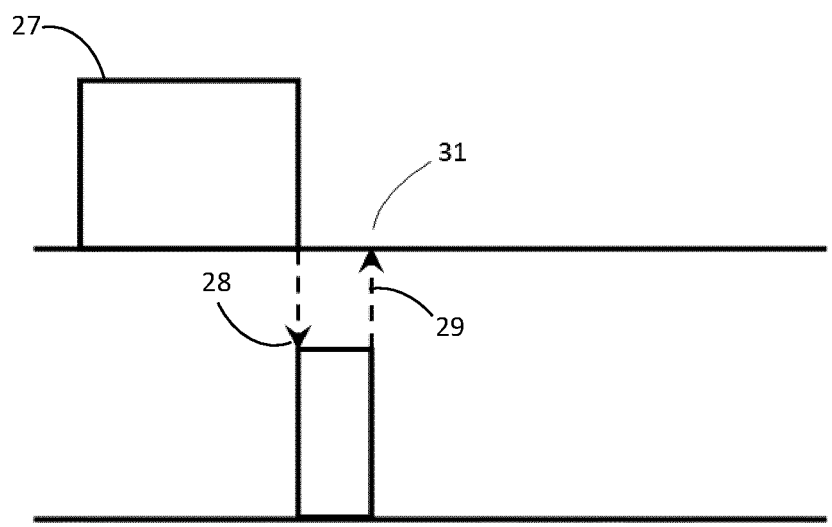

FIGS. 5, 6 and 7 illustrate a reflected power trip test. FIG. 5 is a flow chart illustrating in overview a test method for the reflected power trip test. FIGS. 6 and 7 illustrate power transmitted and/or received in different scenarios.

The generator 101 is connected to the portable test device 110 by connecting the coaxial cable 102 to the first connector 21. At stage 120 of FIG. 5, the generator 101 outputs microwave energy. The switch 3 of the portable test device 110 is set such that energy 10 received from the generator 101 is directed to the attenuator 7. The attenuated power is detected and measured by the detector 6. The applied power is measured by the detector 6 as the signal indicated by 27 in FIGS. 6 and 7.

At stage 122, the switch 3 is activated. The position of the switch 3 is changed such that energy 10 received from the generator 101 is directed into the mismatch 5. The time at which the switch is activated is indicated by 28 on FIGS. 6 and 7.

This signal 27 is present until the switch 3 is activated 28, at which point the signal is no longer observable on the applied power channel and the energy is now routed to the impedance termination or mismatch.

At stage 124, after a period of time the switch is deactivated/returned to its original position. The time at which the switch 3 is deactivated is shown in FIGS. 6 and 7 as time 29. The switch 3 is set such that energy 10 received from the generator 101 is directed to the attenuator 7 and the measurement on the applied power channel is restored.

At stage 126, it is determined whether power is received by the detector 6 after the deactivation 29 of the switch. If the reflected power from the mismatch 5 has caused the generator 101 to trip and therefore to stop outputting power, it may be the case that no power is received by the detector 6 from the generator 101 when the switch 3 is deactivated. If the generator has failed to trip, power may still be received after the switch 3 is deactivated. The switching duration is a time in excess of the response time of the generator to ensure the overall system has sufficient time to respond adequately.

FIG. 6 shows an example in which the reflected power trip test has failed to trip the electromagnetic energy generator/amplifier system resulting in the output power remaining on after the switch is deactivated. The power received by the detector after the deactivation of the switch 29 is indicated by 30 in FIG. 6.

FIG. 7 shows an example in which the reflected power trip test has succeeded in tripping the electromagnetic energy generator/amplifier system resulting in no output power being observed when the switch is deactivated/returned 29 to the measurement of the applied power channel. The absence of a signal on the detector after the switch 3 is deactivated 29 is shown as 31 in FIG. 7.

Figure 8:
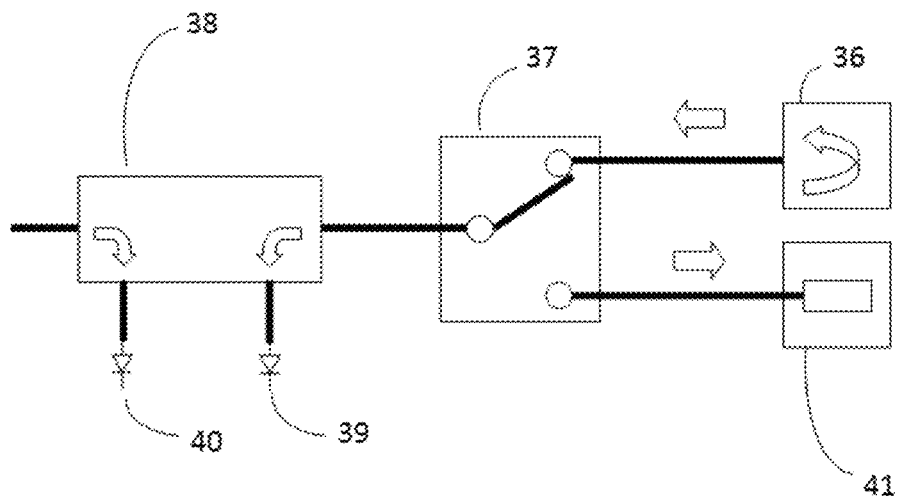
FIG. 8 is a schematic illustration of an alternative arrangement of a reflected power measurement for use with a RF/Microwave ablation system.

An alternative and more typical configuration for a reflected power trip test, which is different to that used in the test method of the present embodiment, is illustrated in FIG. 8. In this illustration a (dual) directional coupler 38 delivers energy to a switch 37 which selects between a mismatch 36 or an absorbing load 41. The forward applied power is sampled by a detector 40 and the reverse reflected power is measured by a detector 39. This arrangement allows for simultaneous measurement of both forward and reverse power at the cost of a number of more bulky and expensive components and may not be as efficient as the method detailed herein.

The portable test device may be able to send commands or signals to the electromagnetic energy generator/amplifier system 101 to start, stop, confirm, disable, reset, delay or otherwise control or manipulate the system 101 to ensure that the desired user functions or behaviours operate as expected.

The portable test device may be able to output device use identity (DUID) that allows automatic setting of test parameters in the system under test (e.g. test mode identity). This may take the form of a current or resistance value created to mimic a specific DUID identity.

The portable test device 110 may be able to identify and diagnose if incorrect parameters such as continuity, voltage, current, resistance, electromagnetic energy, signal timing, identity, audible alerts, visual alerts, visible indicators or other parameters are presented. The device 110 may be able to command the power-on-reset condition or force shutdown of the electromagnetic energy generator/amplifier 101.

The portable test device 110 may be able to return simulated voltages, currents or signals to represent various parameters such as resistance, voltage levels that equate to thermocouple temperatures, product identities, reuse status, connection states and continuity.

The portable test device 110 may be fully automatic. In other embodiments, the portable test device 110 may be able to prompt the test personnel at predetermined stages to act, for example to visually check connections, operation, or performance or to remove or add components to simulate ideal or faulty conditions.

The portable test device 110 may be able to run to conclusion a raft of tests that may be programmed or may be set or selected from a list by test personnel.

The portable test device 110 may be able to adjust settings to correct or modify the hardware performance of the unit or component under test via SPI communications to change hardware DIGIPOT (digital potentiometer) settings, or reprogram other firmware, hardware, or software registers.

The portable test device 110 may be able to adjust settings to correct or modify the software performance of the unit or component under test via SPI communications to change software settings, or reprogram other software, firmware, or hardware registers.

The portable test device either directly or via a mobile hardware application may deliver modified firmware programming to the electromagnetic energy generator/amplifier system 101 or accessories to permit in-field reprogramming based upon diagnostic results. This modified firmware programming may be stored on or delivered to a mobile hardware application or stored on or delivered directly to the portable test device 110 via a network or connection (wireless or connected) to a software database or repository.

The portable test device 110 either directly or via a mobile hardware application may deliver modified software programming to the electromagnetic energy generator/amplifier system 101 or accessories to permit in-field reprogramming based upon diagnostic results. This modified software programming may be stored on or delivered to a mobile hardware application or stored on or delivered directly to the portable test device via a network or connection to a software database or repository.

We consider an example of a test process that is performed by a test operator. The test operator connects the tester 110 to a power source, for example to mains power or a mains power adapter. The test operator connects the generator 101 to a power source, for example to mains power. The operator turns on the tester 110. Indicator lights of the tester 110 turn on and the display 20 of the tester turns on 110.

The operator connects an applicator 104 to the second connection 22. The operator removes a reference disposable tip from the storage compartment 23 and places the tip on the end of the applicator 104.

A reusable transmission cable 102 is connected to the generator 101 at its proximal end. The operator connects the distal end of the reusable transmission cable 102 to the first connection 21 of the tester 110. The operator turns on the generator 101. The operator may also set the generator 101 to an initial value of power output.

The tester 110 performs a set of tests relating to the generator 101, transmission cable 102 and/or applicator 104. The tests may comprise, for example, forward and reflected power tests; simulated conditions such as loads or mismatches; connection tests, signal path integrity tests, communication tests; timing tests, fusing tests and identity tests. The tests may also or alternatively include further tests, for example any tests described above.

In the event of a trip test failure the operator may also be instructed to swap the reusable transmission cable 102 for a known good example and repeat the test to isolate the problem either to their cable or their generator. A similar swap approach may be used for other test failures such as applicator 104 or tip failure. The tester 110 may also be able to carry out a built in self test (BIST) to check the tester 110 is operating as expected.

When the set of tests is completed, the tester 110 outputs a code word on the display 20. This code word may be entered into a website or otherwise communicated to a database for analysis. Each code will be expected to be unique to prevent reuse of codes. This analysis may check validity/integrity of the code, establish proof of a test being run (for financial transactional or traceability reasons for example test certificate or receipt or confirmation) and/or for deciphering and interpretation of the test result to determine status of tests. This interpretation may prompt further instruction or actions to be taken by the operator. For example to remedy the failure, repeat or to complete the test process or to further isolate faults etc. These results and actions may be logged to provide analytical metrics to monitor and improve the test experience.

Figure 9:
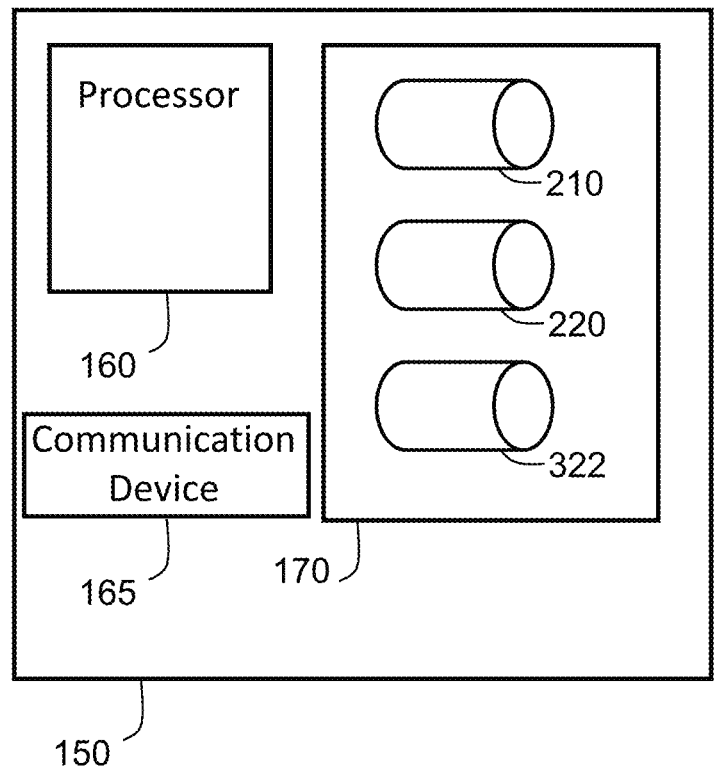
FIG. 9 is a schematic illustration of a computing apparatus.

FIG. 9 is a schematic illustration of a computing apparatus 150, for example a central server, which is configured to provide information to a website and to receive inputs from a user via the website or via other input methods. The computing apparatus 150 comprises a processor 160 comprising processing circuitry configured to perform methods as described below with reference to FIGS. 10a, 10b, 11a, 11b, and 12b. In other embodiments, the methods of FIGS. 10a, 10b, 11a, 11b, and 12b may be performed by any suitable processor or combination of processors. The processor or processors may form part of any suitable computing apparatus or apparatuses. The processor may host a virtual machine, website application, any language of computer code (machine code or assembly language) or any higher level software language or script to interpret information or provide calculations or computations.

The computing device 150 further comprises a communication device 165 which is configured to transmit data to, and receive data from, further computing apparatuses. The communication device 165 may provide data communication using any suitable method or methods, for example a wired internet connection, a wireless method such as Bluetooth®, WIFI™, Zigbee®, or WIMAX®, or communication with mobile networks such as GSM™, UMTS, CDMA2000, LTE, 3G, 4G, or 5G.

The computing apparatus 150 of FIG. 9 further comprises a data store 170 which is configured to store a healthcheck calendar database 210, a customer database 220, and a healthcheck database 322. In other embodiments, the data store 170 may store any suitable data in any suitable format, for example in any suitable combination of databases or other storage structures. In further embodiments, the databases 210, 220, 322 may be stored in any suitable data store or data stores, which may form part of any suitable computing apparatus or apparatuses.

Figure 10A:
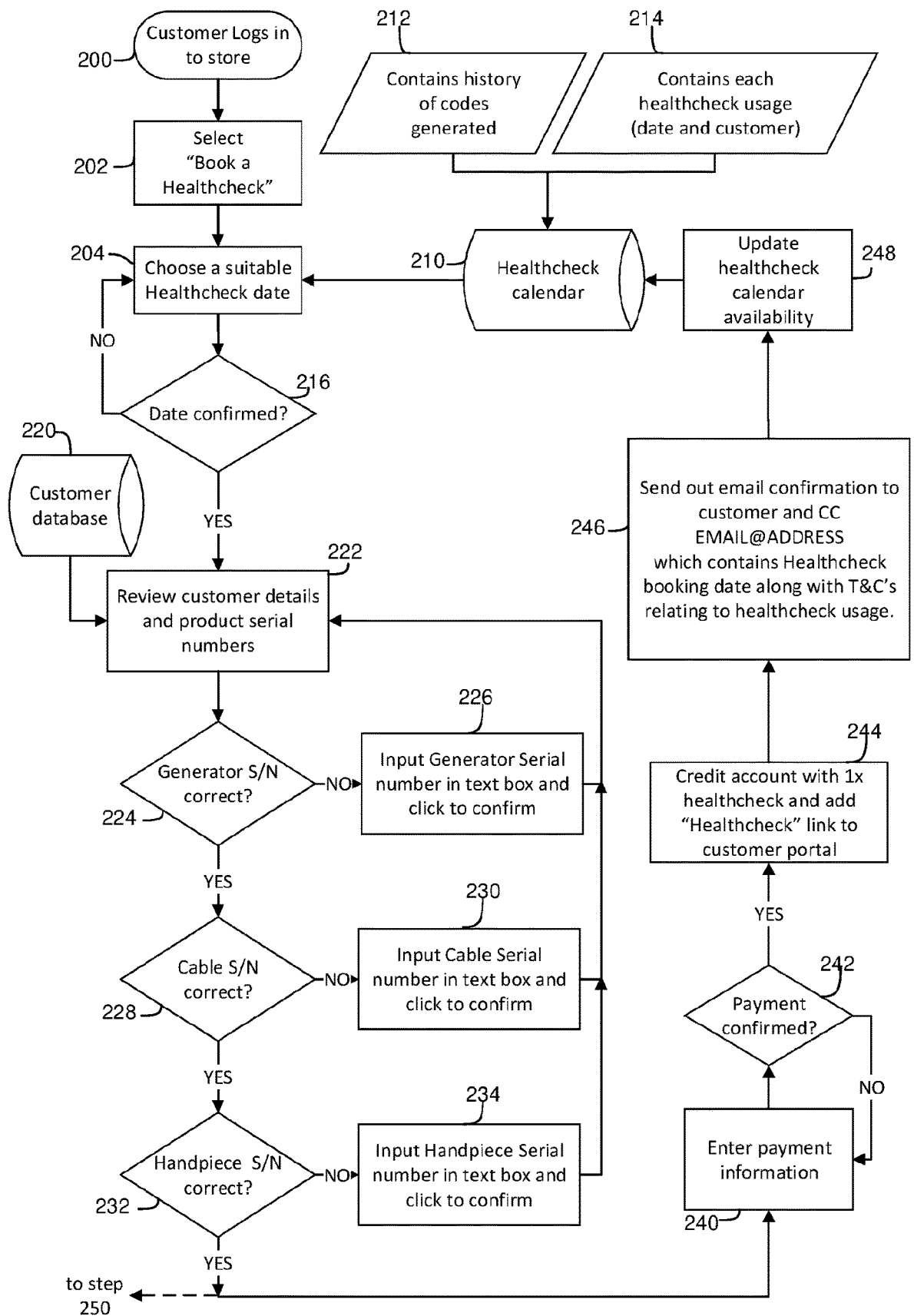
FIGS. 10a and 10b are flow charts representing in overview a process for booking a test.

FIG. 10a is a flow chart illustrating in overview a first part of a booking method in accordance with an embodiment. A second part of the booking method of the embodiment is illustrated in overview in FIG. 10b.

The booking method is a method of booking a healthcheck test. The healthcheck test may comprises a test of a generator 101 and/or a coaxial cable 102 and/or a reusable handpiece 103 and/or an applicator 104. The applicator 104 may comprise a single-use disposable tip.

The healthcheck test may comprise any one or more of the tests described herein. The healthcheck test may comprise testing that is performed on site, for example at a customer premises, rather than the device to be tested being returned to a factory or service centre. The healthcheck test may be performed using a portable test apparatus 110 as described above.

Actions described below are described as being performed by a customer. In other embodiments, the actions may be performed by any user or users, who in some circumstances may not be a customer. For example, some or all of the actions may be performed by a technician operating the portable test apparatus 110.

At stage 200, a customer logs in to a store. For example, the customer may log into an online store provided as a website. The customer-accessible online store may be referred to as a customer portal. The customer may login to the website using the customer's own computing apparatus (not shown), for example using a mobile device. Alternatively, the customer may login using any suitable device. The processor 160 receives information regarding the customer's login via the communication device 165. Any subsequent inputs provided by the customer via the website may also be received by the processor 160 via the communication device 165. In other embodiments, the processor may receive information from the customer using any suitable communication method.

At stage 202, the customer selects 'Book a Healthcheck' on the website. At stage 204, the customer chooses a suitable Healthcheck date on the website, for example by choosing one of a plurality of selected dates. The processor 160 receives information about the requested booking and date via the communication device 165. The processor further receives data from the healthcheck calendar database 210. The healthcheck calendar database 210 comprises a history of codes generated 212 and each details of each healthcheck that has been performed 214. The healthcheck calendar database 210 further comprises information about available dates on which a healthcheck may be performed.

At stage 216, the processor 160 compares the date requested by the customer at stage 204 and the dates available in the healthcheck calendar 210. If the date requested by the customer is available, the processor 160 determines that the date is confirmed and the process of the flow chart proceeds to stage 222. If the date requested by the customer is not available, the flow chart returns to stage 204 and the processor 160 issues instructions to the website to ask the customer to select another date. Once the customer has selected another date, the flow chart repeats stage 216.

Once a date has been confirmed at stage 216, the flow chart proceeds to stage 222. At stage 222, the processor receives the confirmed date, and the flow chart further receives data from a customer database 220. The customer database 220 is further illustrated in FIG. 10b. The customer database 220 comprises generator serial numbers 262, cable serial numbers 264, and handpiece serial numbers 266. Each of the generator serial numbers 262, cable serial numbers 264, and handpiece serial numbers 266 may be associated with a respective customer. The customer database 220 further comprises a healthcheck history and full service history. The healthcheck history and full service history may comprise dates on which healthcheck tests were performed, codes that were generated by healthcheck tests, and decoded information that was obtained from codes generated by healthcheck tests. Similar information may be provided for full service tests. The customer database 220 further comprises a history of a customer's serial numbers for a product, for example generator serial numbers, cable serial numbers and/or handpiece serial numbers.

At stage 222, the processor 160 retrieves from the customer database 220 details of the customer that logged in at stage 200. The processor 160 retrieves from the customer database 220 details of product serial numbers associated with the customer. The product serial numbers comprise at least one generator serial number, at least one cable serial number, and at least one handpiece serial number.

At stage 224, the processor 160 instructs the website to display to the customer a generator serial number. The customer determines whether the displayed generator serial number is correct. If the generator serial number is incorrect, the process proceeds to stage 226. At stage 226, the customer inputs the correct generator serial number in a text box of the website and clicks to confirm. In other embodiments, any suitable input method may be used to obtain the correct generator serial number. The process returns to stage 222 and to stage 224. If the generator serial number is correct at stage 224, the process proceeds to stage 228.

At stage 228, the processor 160 instructs the website to display to the customer a cable serial number. The customer determines whether the displayed cable serial number is correct. If the cable serial number is incorrect, the process proceeds to stage 230. At stage 230, the customer inputs the correct cable serial number in a text box of the website and clicks to confirm. In other embodiments, any suitable input method may be used to obtain the correct cable serial number. The process returns to stage 222, to stage 224 and to stage 228. If the cable serial number is correct at stage 228, the process proceeds to stage 232.

At stage 232, the processor 160 instructs the website to display to the customer a handpiece serial number. The customer determines whether the displayed handpiece serial number is correct. If the handpiece serial number is incorrect, the process proceeds to stage 234. At stage 234, the customer inputs the correct handpiece serial number in a text box of the website and clicks to confirm. In other embodiments, any suitable input method may be used to obtain the correct handpiece serial number. The process returns to stages 222, 224, 229 and 232. If the cable serial number is correct at stage 232, the process proceeds to stage 240 and stage 250 (shown on FIG. 10b).

The customer may be asked to confirm that each serial number is correct in any suitable manner, for example by clicking on a button. In the embodiment of FIG. 10a, the customer is requested to confirm each of the generator serial number, cable serial number and handpiece serial number individually. In other embodiments, the customer may perform a single action (for example, clicking a single button) to confirm all serial numbers. In further embodiments, the generator serial number, cable serial number and/or handpiece serial number may be displayed to the customer in any order and may be confirmed by the customer in any order, using any suitable input method.

At stage 240, the customer enters payment information into the website. At stage 242, a confirmation process occurs in which the payment is confirmed or is not confirmed. The confirmation process may be performed by the processor 160 or by a further computing apparatus. For example, the confirmation process may be performed by an external payment provider. If the payment is not confirmed, the process returns to stage 240 and the customer enters different payment information. If the payment is confirmed, the process proceeds to stage 244.

At stage 244, the processor 160 credits an account associated with the customer with one healthcheck. The processor 160 adds a 'Healthcheck' link to the customer portal.

At stage 246, the processor 160 instructs the automatic sending of an email confirmation to the customer. The email contains the healthcheck booking date that was confirmed at stage 216. The email further contains terms and conditions relating to usage of the healthcheck. The email is copied to an internal email address used by the provider of the healthcheck function, for example a manufacturer or provider of the generator 101 and/or cable 102 and/or handpiece 104 and/or portable test apparatus 110. The internal email address is indicated in the flowchart as EMAIL@ADDRESS.

In other embodiments, information regarding the healthcheck booking and/or information regarding the contact to the customer may be sent by internal email address and/or by any suitable alternative communication means, for example by a connection or message to an internal ERP (enterprise resource planning) system, CRM (customer relationship management) system, or database. Any suitable system or function of the computing apparatus 150 or of a further computing apparatus or system may be alerted that the customer has been contacted.

At stage 248, the processor 160 updates the healthcheck calendar availability in the healthcheck calendar database 210.

Figure 10B:
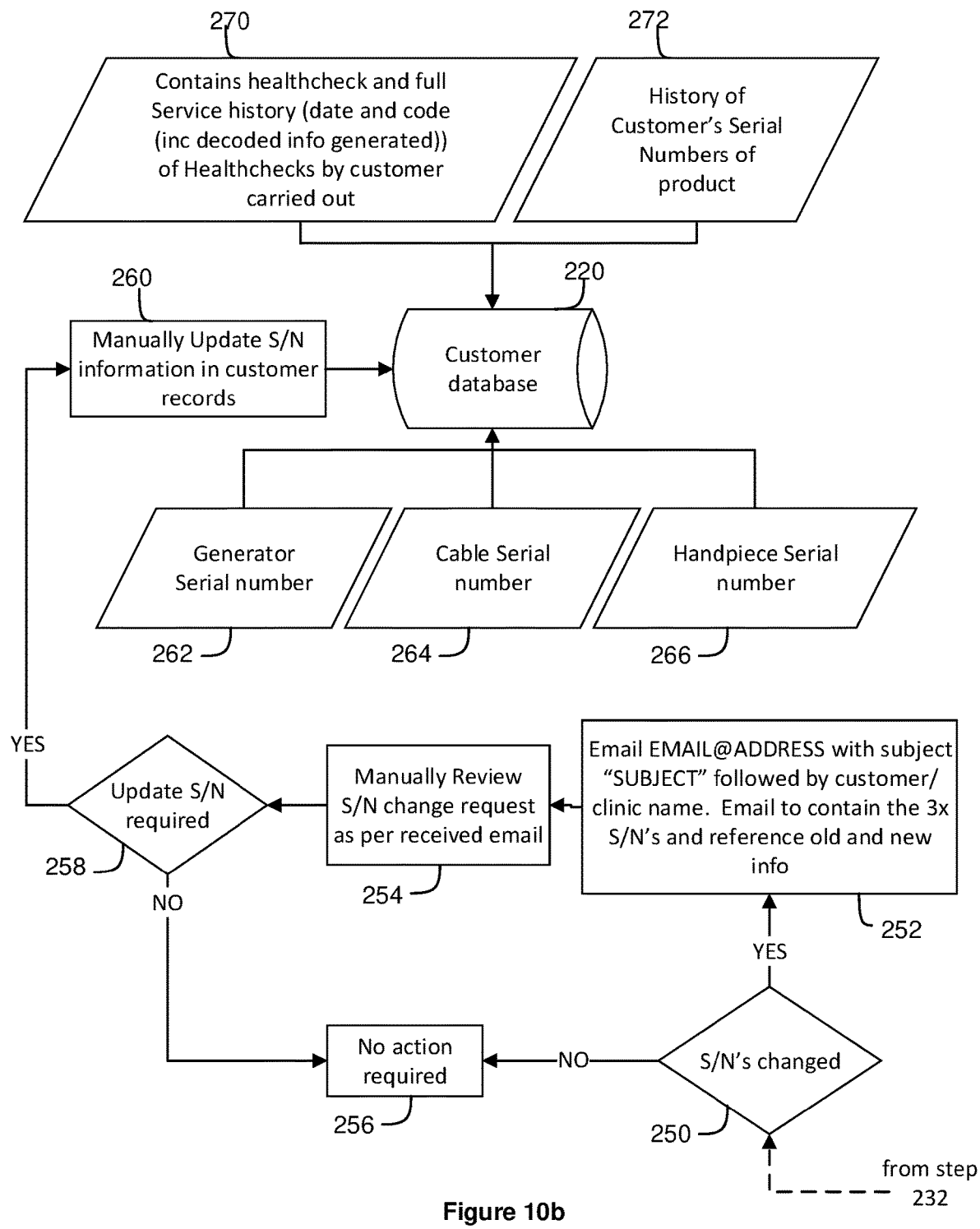

Turning to FIG. 10*b*, once all of the generator serial number, cable serial number and handpiece serial number are confirmed, the process also proceeds to stage 250 as illustrated in FIG. 10*b*.

At stage 250, the processor 160 assesses whether any of the serial numbers has been changed when compared with the serial numbers that were previously held in the customer database. For example, the serial numbers may be have changed by customer input at stages 226, 230 and/or 234. If no serial numbers have changed, the process proceeds to stage 258. If any of the generator serial number, cable serial number, and handpiece serial number has changed, the processor instructs the sending of an email to the internal address shown as EMAIL@ADDRESS. The email has the subject "SUBJECT" followed by a name of the customer and/or a name of an organisation with which the customer is associated, for example a clinic. The email contains both old and new values for the generator serial number, the cable serial number, and the handpiece serial number. In other embodiments, any suitable system or function of the computing apparatus 150 or of a further computing apparatus or system may be provided with information regarding the old and/or new serial numbers, by any suitable communication means.

At stage 254, an employee of the healthcheck test provider manually reviews the change of one or more of the serial numbers. The employee assesses whether it is required to update the serial numbers held in the customer database 220. At stage 258, if no update to the serial numbers held in the customer database 220 is required, the process proceeds to stage 256 and no action is taken. If an update is required, the process proceeds to stage 260. At stage 260, an employee of the healthcheck provider manually updates one or more of the generator serial number, cable serial number, and handpiece serial number in a record associated with the customer. The manual update is applied to the customer database 220. In other embodiments, any suitable method may be used for updating the generator serial number and/or cable serial number and/or handpiece serial number. The method of updating may be manual or automated.

Figure 11A:
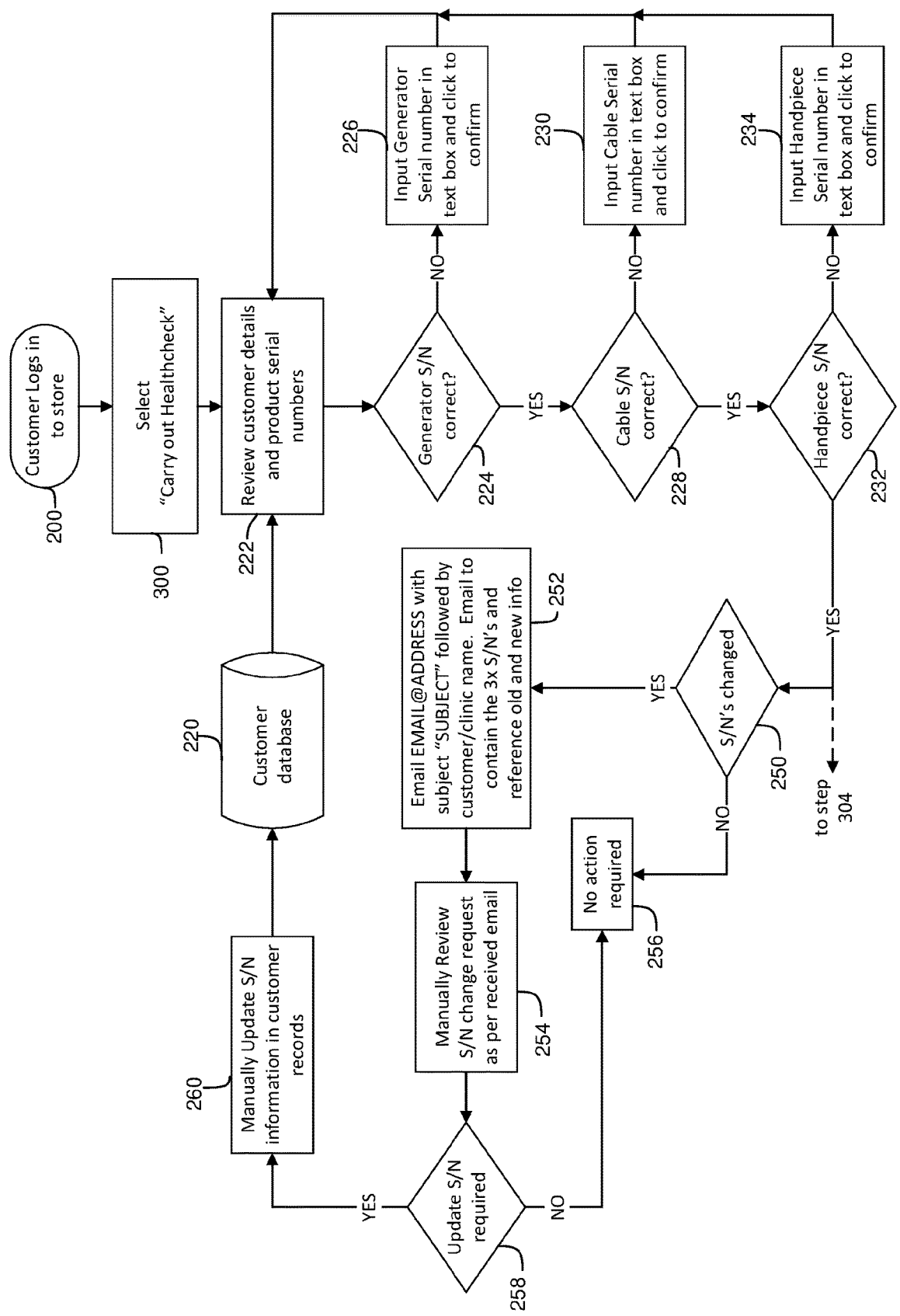
FIGS. 11a and 11b are flow charts representing in overview a process for performing a test.

FIG. 11*a* is a flow chart illustrating in overview a first part of a healthcheck test method in accordance with an embodiment. A second part of the method of the embodiment is illustrated in overview in FIG. 11*b*.

Figure 11B:
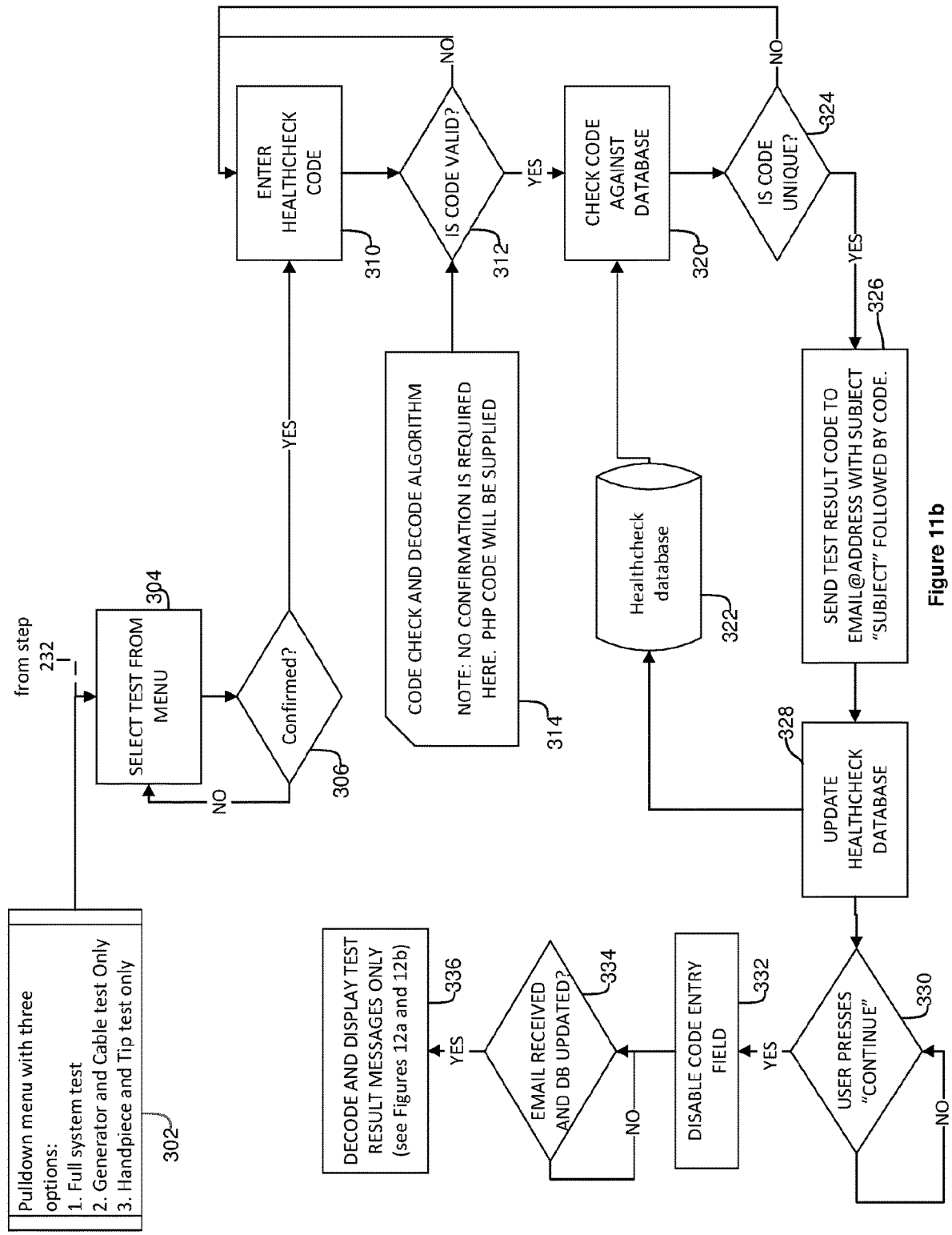

In the method of FIGS. 11*a* and 11*b*, a user inputs details of a device that has been tested using the portable test apparatus 110 as described above, and provides a healthcheck code that is output by the portable test apparatus 110. The healthcheck test may be performed by any appropriate individual, for example a customer or a technician. The processor 160 validates and analyses the healthcheck codes. Details of the decoding and display of test results are described below with reference to FIGS. 12*a* and 12*b*.

Turning to stage 200 of FIG. 11*a*, the customer logs in to the store website as described above with reference to FIG. 10*a*. At stage 300, the customer selects on the website an option of 'Carry out Healthcheck'. The flow chart then proceeds to stages 222, 224, 226, 228, 230, 232, 234, 250, 252, 254, 256, 258 and 260, which are the same as described above in relation to FIG. 10*a*.

Once all of the generator serial number, cable serial number and handpiece serial number are confirmed to be correct at stages 224, 228 and 232 respectively, the process proceeds to stage 250 and also to stage 304, which is illustrated in FIG. 11*b*.

The user performs the healthcheck test using the portable test apparatus 110. The healthcheck test may be a full system test, which tests the generator, cable, handpiece and tip. The healthcheck test may be a test of the generator and cable only. The healthcheck test may be a test of the handpiece and tip only. The portable test apparatus 110 may also be referred to as a healthcheck apparatus, or healthcheck hardware.

The user may perform the healthcheck test using the portable test apparatus 110 after the serial numbers have been input. Alternatively, the user may perform the healthcheck test before, or in parallel with, the inputting of the serial numbers.

Turning to FIG. 11*b*, at stage 302 the processor 230 instructs display of a pulldown menu to the user on the website. The pulldown menu shows three options for a healthcheck test. A first option is a full system test. A second option is a test of a generator and cable only. A third test is a test of a handpiece and tip only.

At stage 304, the user selects one of the three options from the pulldown menu. The user selects the option that corresponds to the healthcheck test that has been run by the user. The processor 160 receives the selection of the one of the three options.

At stage 306, the user is asked to confirm the test selection. The user confirms the test selection, or selects a different option. If the test selection is confirmed by the user, the process proceeds to stage 310.

At stage 310, the user enters a healthcheck code into a healthcheck code entry field of the website. The healthcheck code is output by the portable test apparatus 110 as described above.

The selection and confirmation of a healthcheck test option by the user at stages 302 and 304 informs the software as to how to interpret the software correctly. In some circumstances, an incorrect selection of tests used could result in an incorrect interpretation of the encoded results. In further embodiments, the processor 160 may check all possible sets of results (for example, the results that would be obtained if full system test was selected; if generator and cable test was selected; and if applicator and tip was selected). The processor 160 may determine whether the data being reported for each test result is sensible data for the test result, for example if it falls into an expected range of results. The expected range of results may include both pass and fail results. If the option selected by a user does not produce sensible results, the processor 160 may instruct an alert to the user that the option selected may be incorrect.

In the present embodiment, the user reads the healthcheck code from the display area 20 of the portable test apparatus 110 and enters the healthcheck code manually in the healthcheck code entry field manually. In other embodiments, any suitable method for capturing the healthcheck code may be used, for example methods as described above such as using a camera or using a wired or wireless connection.

The healthcheck code may comprise at least one binary word and/or at least one hexadecimal word and/or at least one multi-letter language word, as described above.

At stage 312, the processor 160 determines whether the healthcheck code that has been entered is valid. The processor 160 uses an algorithm 314 that is configured to check and decode the healthcheck code. In the present embodiment, the algorithm 314 is implemented by a PHP (Hypertext PreProcessor) script. The PHP script that runs the algorithm 314 is held in a secure part of the website. The PHP script executes commands and returns data only. The PHP script cannot be viewed, read, copied or disassembled, for example by the user.

If the code is determined not to be valid at stage 312, the process returns to stage 310 for a new healthcheck code to be entered. Alternatively, the existing healthcheck code may be edited by the user.

If the code is determined to be valid at stage 312, the process proceeds to stage 320. At stage 320, the processor 160 receives the valid code. The processor 160 also receives information from the healthcheck database 322. The healthcheck database 322 comprises codes obtained from previous healthcheck tests.

At stage 324, the processor 160 compares the healthcheck code to previous codes and determines whether the code is unique. If the code is not unique, the process returns to stage 310 for the customer or other user to re-enter or edit the healthcheck code.

If the code is determined to be unique, the process proceeds to stage 326. At stage 326, the processor 160 instructs the sending of an email to EMAIL@ADDRESS. The subject line of the email is "SUBJECT" followed by the healthcheck code. In other embodiments, any suitable system or function of the computing apparatus 150 or of a further computing apparatus or system may be provided with the code and/or with information regarding the code, by any suitable communication means.

At stage 328, the processor 328 updates the healthcheck database 322 to include the healthcheck code. The process proceeds to stage 330. At stage 330, the customer or other user presses 'Continue' on the website. Until the user has pressed continue, the process waits at stage 330.

At stage 332, once the customer or other user has pressed 'Continue', the processor 160 instructs the healthcheck code entry field of the website to be disabled.

At stage 334, the processor 160 determines whether the email of stage 326 has been received and the healthcheck database 322 has been updated. If not, the process waits until the email has been received and the healthcheck database 322 has been updated.

If the email has been received and the healthcheck database 322 has been updated, the process proceeds to stage 336. At stage 336, the processor 160 decodes and displays the results of the healthcheck test for which the healthcheck code has been provided. The decoding and display process is described below with reference to FIGS. 12a and 12b.

In the decoding and display process, the user is provided only with pass or fail results. The user is not given detailed numerical information on the test results, for example parameter values. Detailed numerical information on the test results is extracted from the healthcheck code and is stored by the healthcheck test provider. Healthcheck test result information may be stored in the healthcheck database 322 and/or in the customer database or in any suitable database. Test result information may be stored against each customer's profile. Test result information may be inspected by the healthcheck test provider, for example for engineering or quality assurance purposes.

The user is only provided with the pass/fail summary and does not have any means to determine the exact results or how the tests are constructed, or to reverse the hidden code.

FIG. 12a is a list of test results that may be encoded in the healthcheck code. Each line of the list comprises a bit number followed by a type of signal. The bit numbers are represented by ##, since any appropriate amount of bit numbers may be used.

In the embodiment shown in FIG. 12a, tests include measuring device use identity (DUID_measured). The tests include a first power test (Reflected_Power_Test(1)). The first power test may measure power being delivered into a match. The measured power may comprise values for at least one of peak power, average power, pulse width modulation (PWM). The PWM duty cycle is measured by sampling a time portion of the modulated microwave signal (e.g. rectified voltage) and measuring the mark to space ratio within the modulation. This could also be a subtraction measurement of the ON time duration or OFF time duration if the pulse duration is fixed or known.

Values for PWM may comprise values for duty cycle and/or frequency. The first power test checks whether the power is as expected, to confirm that the microwave generator 101 is operating correctly and the healthcheck is working correctly. By having PWM and peak it can be determined if there is a coaxial cable issue (PWM is as expected and power is low), a generator issue (PWM is not as expected and power is not as expected), or a healthcheck issue (no PWM or power).

The tests include a test that checks that a Green LED drive line is being pulsed (Generator_Green_Drive_Detected). The pulsing of the Green LED drive line indicates that the generator 101 can identify a suitable DUI D presented by the healthcheck and is ready for use. It confirms this state and also checks that the associated wiring in the cable 102 can communicate this state.

The tests include a test of a handpiece button (HP_Button), a test of whether the cable 102 is connected (Cable_Connected), a test of generator fusing current (Generator_Fusing_Current), a test of illumination of a green ring on the handpiece (HP_Green_Ring_Sensed), and a test of whether the handpiece is connected (Handpiece_Connected).

The tests include second power test (Reflected_Power_Test(0)). The second power test measures power being delivered (peak, average and/or PWM) once the mismatch 5 is invoked by energy being directed to the mismatch 5. The second power test confirms whether the portable test apparatus 110 is working properly. The power should be very low or none measured, because the detector 6 should have no signal.

The tests include a test of whether a tip is connected (Tip_Connected).

The tests include a test of illumination of a yellow ring on the handpiece (HP_Yellow_Ring_Sensed) and a test of coaxial resistance of the handpiece (Handpiece_Coax_Resistance_Sensed).

The tests include a test of a yellow LED (Generator_Yellow_Drive_Detected). This test checks that a Yellow LED is active which indicates that the generator 101 has not identified a suitable DUID (device ID) and is therefore not ready for use. It confirms this state and also checks that the associated wiring in the cable can communicate this state.

The tests include a test of generator fusing (Generator_Fusing_Detection).

The tests include a test of microwave power after a reflected power condition to determine if output power is still present (No_MW_Power_Post_RP). Is output power is still present, a value for No_MW_Power_Post_RP is set to 0. If no output power is still present, a value for No_MW_Power_Post_RP is set to 1. A value of 1 indicates that the microwave generator 101 has detected the reflected power condition and correctly deactivated the output power. This test also indirectly confirms that the microwave cable 102 is functional and capable of delivering a suitable level of incident power and returning a suitable level of reflected power to enable the generator to check for reflected power. Any damage to the cable could attenuate this signal and the test could therefore fail.

The tests include a test of internal temperature of the portable test apparatus 110 (Internal temperature (healthcheck)). In other embodiments, any suitable tests may be included. The tests may relate to any or all of the generator 101, cable 102, handpiece 103 and tip 104.

A binary result (1 or 0) may be provided for each of the test to indicate whether the test has been passed or failed.

In the present embodiment, further optional tests include tests that are indicated in the list of FIG. 12a as External thermocouple temperature TC1/Trip, External thermocouple temperature TC2/Trip, Pump speed sensed and Acoustic signals sensed.

The portable test device 110 may be configured to sense acoustic signals to sense, for example, a fan frequency and/or at least one beep sequence. Temperature of the tester unit may be tested. Thermocouple trip tests may be performed. For example, a thermocouple measurement may be obtained as power is driven into the generator 101 from the portable test device 110 to cause a trip, either to measure the power level or to confirm the action.

The generator 101 may have a function that could trip the power or treatment off when a particular external temperature is measured. For example, the power or treatment may be tripped off in response to external temperature of 43° C. or 44° C., for example to reduce or avoid tissue damage. It may be of use to be able to confirm this function is operating within specification (using the health check) as this function may be a safety feature of the medical device.

The portable test device 110 may be configured to sense at least one parameter of at least one ancillary component. For example, the portable test device 110 may be configured to test a speed of a pump.

In other embodiments, the tests may comprise any suitable test. For example, the portable test device 110 may be configured to perform a test of SPI communications. The tests may comprise a validation check. The test may comprise a test of unique codeword.

It is noted that the tester 110 creates a unique codeword by combining measurements that may be considered to provide more random or unpredictable results, for example power, temperature and/or usage. Validity of the codeword may be checked by examining a parity checksum bit that is used to hash the overall codeword.

Figure 12B:
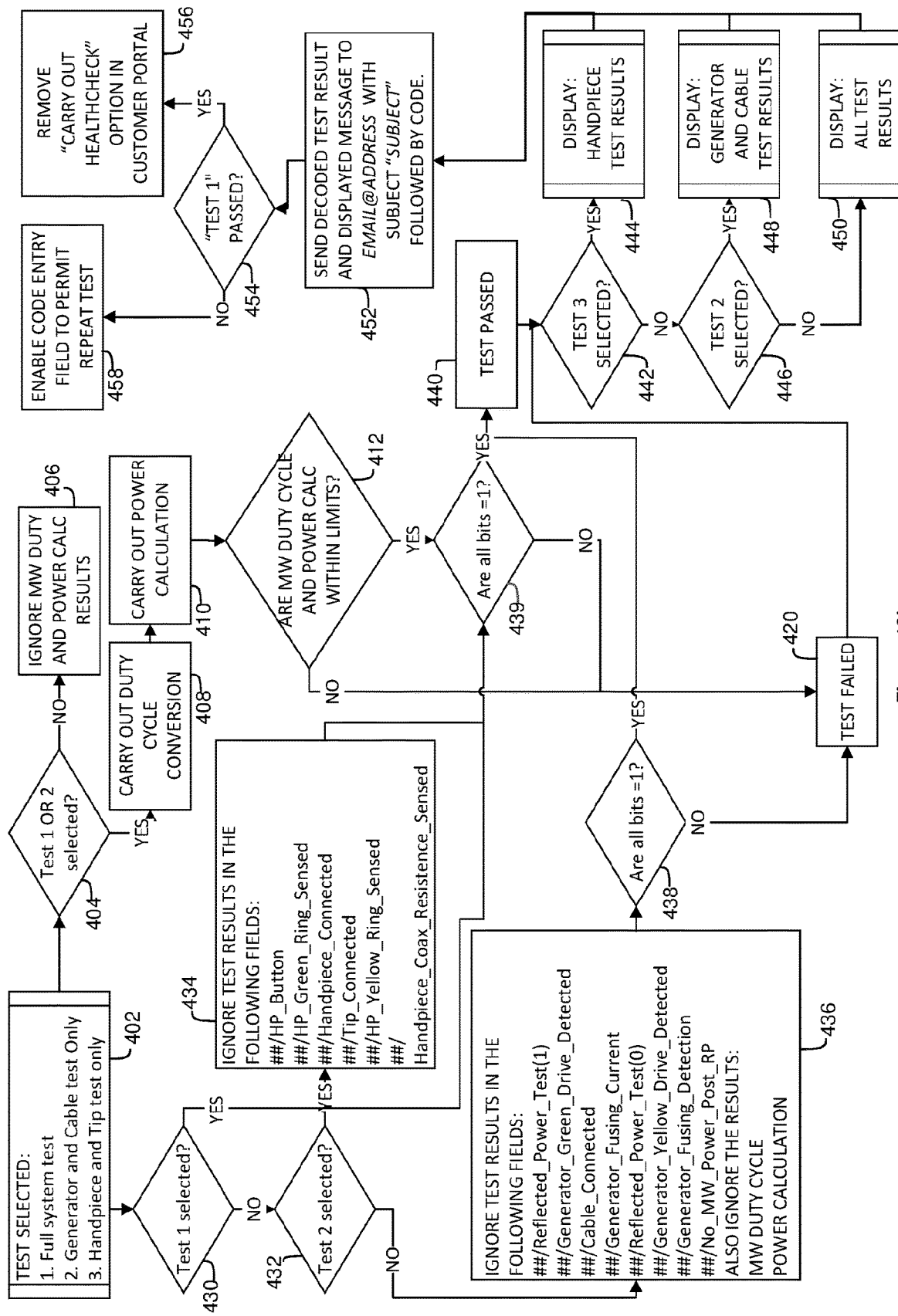
FIG. 12b is a flow chart illustrating in overview a method of generating and displaying test results.

FIG. 12b is a flow chart illustrating in overview a method of decoding and displaying test results. Before the method of FIG. 12b is carried out, the healthcheck code itself has been decoded to obtain a set of healthcheck results, for example results for the parameters listed in FIG. 12a.

As described above, three types of healthcheck test are available. The first (test 1) is a full system test. The second (test 2) is a test of the generator 101 and cable 102 only. The third (test 3) is a test of the applicator handpiece and tip only.

The processing of the test results varies in dependence on the test shown. If test 2 or test 3 is chosen, certain of the test results are ignored.

Turning to FIG. 12b, stage 402 is a test selection stage at which the processor 160 receives a selection of test 1, test 2 or test 3. Stage 402 may correspond to stage 304 of FIG. 11b.

At stage 404, the processor 160 determines whether test 1 or test 2 has been selected. If neither test 1 nor test 2 has been selected, the method proceeds to stage 406, at which the processor 160 ignores MW duty and power calculation results. If test 1 or test 2 has been selected, the method proceeds to stage 408. At stage 408, the processor 160 carries out a duty cycle conversion 500.

Figure 13:
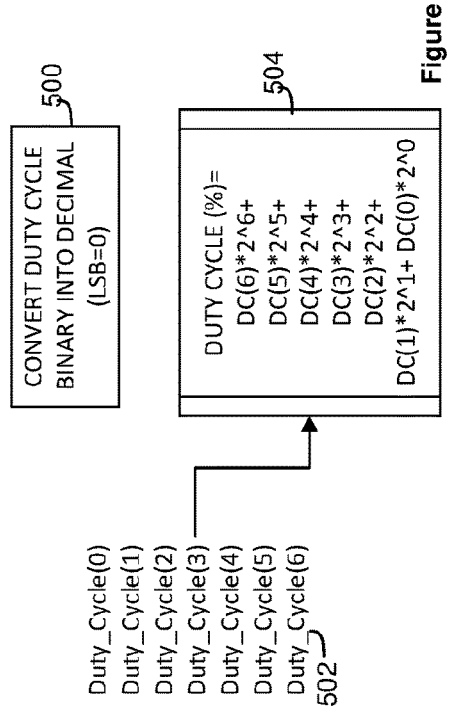
FIG. 13 is a flow chart illustrating in overview a duty cycle calculation.

The duty cycle conversion 500 is illustrated in FIG. 13. A hexadecimal value set encoded in the healthcheck code 310 is recovered to provide a binary word representing the duty cycle. The duty cycle conversion 500 comprises converting the binary value for duty cycle into a decimal value. The least significant bit is at position 0. The duty cycle conversion 500 is illustrated by showing an input 502 and the calculation of an output value 504. The input 502 comprises values for bits 0 to 6 of a binary value that is representative of duty cycle. The bits are labelled as Duty_Cycle(0) to Duty_Cycle(6). At stage 504, the processor 160 performs a calculation to obtain a decimal value for duty cycle, as a percentage. The processor 160 uses the equation:

$$\text{DUTY CYCLE (\%)} = DC(6)*2^6 + DC(5)*2^5 + DC(4)*2^4 + DC(3)*2^3 + DC(2)*2^2 + DC(1)*2^1 + DC(0)*2^0$$

in which Duty_Cycle(0) is abbreviated as DC(0), Duty_Cycle(1) is abbreviated as DC(1), and so on.

In other embodiments, any suitable representation of duty cycle may be used in the healthcheck code, and any suitable method of converting the duty cycle in the code to a decimal (or other) value may be used.

Figure 14:
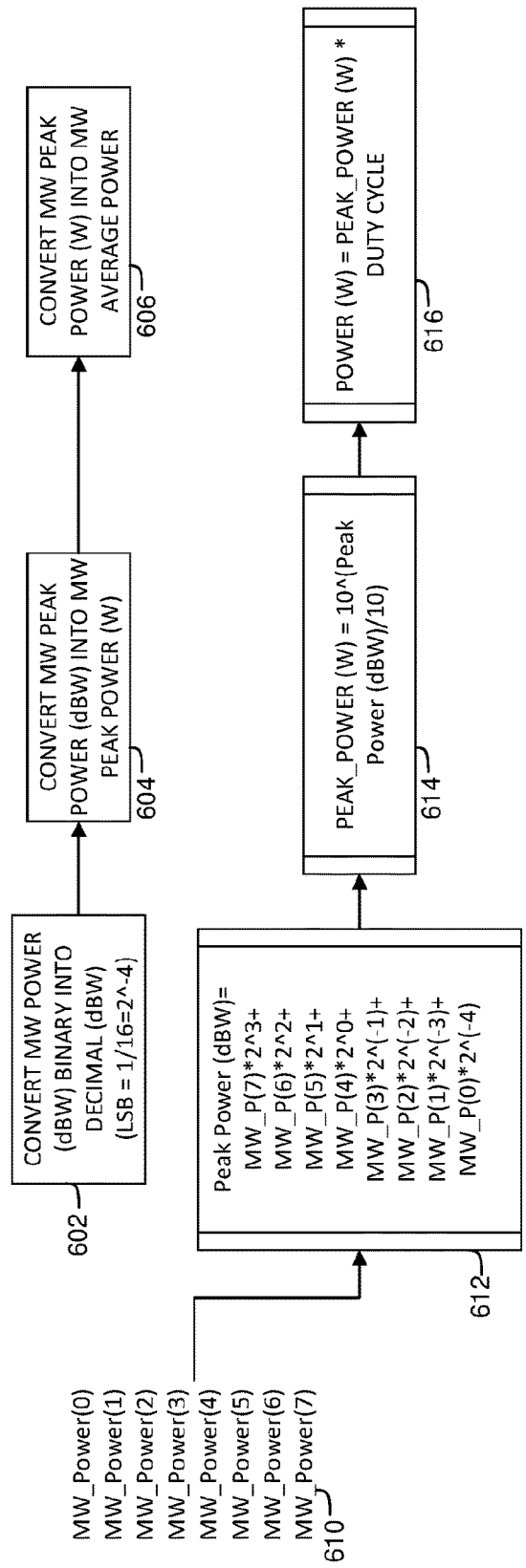
FIG. 14 is a flow chart illustrating in overview a power calculation.

Turning back to FIG. 12b, once the duty cycle conversion 500 has been performed, the method proceeds to stage 410. At stage 410, the processor 410 carries out a power calculation. The power calculation is illustrated in FIG. 14. A hexadecimal value set encoded in the healthcheck code 310 is recovered to provide a binary word representing the peak power. The power calculation comprises a first stage 602 in which MW power in dBW expressed as a binary value is converted into a decimal value (still in dBW). The least significant bit is representative of $1/16 = 2^{-4}$. The power calculation further comprises a second stage 604 in which MW power in dBW is converted into MW peak power in W. The power calculation further comprises a third stage 606 in which the MW peak power in W 604, 614 is converted into MW average power 606, 616 by using the duty cycle information 504.

An input 610 to the first stage comprises values for bits 0 to 7 of a binary value that is representative of MW power in dBW. The bits are labelled as MW_Power(0) to MW_Power (7).

A calculation 612 is used to convert binary into decimal at stage 602. The calculation 612 uses the equation:

$$\begin{aligned}\text{Peak Power }(dBW) = &\text{ MW\_P}(7)*2^{\wedge}3 + \text{MW\_P}(6)*2^{\wedge}2 + \\ &\text{MW\_P}(5)*2^{\wedge}1 + \text{MW\_P}(4)*2^{\wedge}0 + \text{MW\_P}(3)*2^{\wedge}(-1) + \\ &\text{MW\_P}(2)*2^{\wedge}(-2) + \text{MW\_P}(1)*2^{\wedge}(-3) + \text{MW\_P}(0)*2^{\wedge}(-4)\end{aligned}$$

where MW_Power(0) is abbreviated as MW_P(0), MW_Power(1) is abbreviated as MW_P(1), and so on.

A calculation 614 is used to convert MW peak power in dBW to MW peak power in W at stage 604. Calculation 614 uses the equation:

PEAK_POWER (W)=10^(Peak Power (dBW)/10)

A calculation 616 is used to convert MW peak power (W) into MW average power at stage 606. Calculation 616 uses the equation:

POWER(W)=PEAK_POWER (W)*DUTY CYCLE where the value for DUTY CYCLE is the value obtained using the calculation 504 of stage 408 and FIG. 12.

Turning again to FIG. 12b, once the power calculation of stage 410 has been performed, the method proceeds to stage 410. At stage 410, the processor 160 determines whether the MW duty cycle calculated at stage 408 and the power calculation of stage 410 are within predefined limits for duty cycle and power respectively.

If the duty cycle is outside the predefined limits and/or the power calculation is outside the predefined limits, the method proceeds to stage 420, at which it is determined that a test has been failed.

If the duty cycle is within its predefined limits and the power calculation is within its predefined limited, the method proceeds to stage 439.

In other embodiments, the portable test apparatus 110 may directly make the calculation 616 internally using analogue or digital hardware, firmware or embedded software, to multiply the duty cycle data and the peak power measurements and report the average power result via the codeword. The raw measured values only may be communicated or alternatively only the result may be communicated or both.

The portable test apparatus 110 measures and samples signals. In some embodiments, the portable test apparatus 110 performs a power calculation internally. The portable test apparatus may then output results of the power calculation via the code word. In some embodiments, the portable test apparatus 110 outputs a power calculation result may be output without outputting power and/or duty cycle. In other embodiments, raw data is output which includes power values and duty cycle values as encoded. The calculation is then performed externally, for example on or in the website which decodes the data from the codeword and performs the calculation.

By using an external calculation (website, software, external hardware or firmware) based upon the raw measured data, independent enhancements to the measurement can be made offline without the requirement to update the hardware which may be predominately in use. The details of the calculation may be changed centrally instead of being changed on each portable test apparatus 110. This capability can extend to any measurement herein where raw data is reported and an external means is used to determine a test outcome or to calculate a result based upon one or a number of data elements communicated from the test hardware.

Returning to the test selection of 402, in addition to determining whether test 1 or 2 has been selected at stage 404, the processor 160 determines whether test 1 has been selected at stage 430. If test 1 has been selected, the method proceeds from stage 430 to stage 439.

At stage 439, the processor 439 determines whether all bits are 1. The bits in this case are representative of each of the test results. If a test is passed, its bit is set as 1. If a test is failed, its bit is set as 0.

If it is not the case that all bits are equal to 0, the method proceeds to stage 420. At stage 420, the processor 160 determines that the test has been failed.

If all bits are equal to 0 at stage 439, the method proceeds to stage 440. The processor 160 determines that the test has been passed.

Returning to stage 430, if the answer to whether test 1 has been selected is no, the method proceeds to stage 432. At stage 432, the processor 160 determines whether test 2 has been selected. If the answer at stage 432 is yes, the method proceeds to stage 434. The processor 160 ignores test results in the following fields: HP_Button, HP_Green_Ring_Sensed, Handpiece_Connected, Tip_Connected, HP_Yellow_Ring_Sensed, Handpiece_Coax_Resistance_Sensed.

The test results that are ignored at stage 434 are test results pertaining to the handpiece 103 or tip 104. These test results are ignored because test 2 relates only to the generator 101 and cable 102. After stage 434, the method proceeds to stage 439.

If at stage 432, the answer to whether test 2 has been selected is no, the method proceeds to stage 436. At stage 436, the processor 160 ignores test results in the following fields: Reflected_Power_Test(1), Generator_Green_Drive_Detected, Cable_Connected, Generator_Fusing_Current, Reflected_Power_Test(0), Generator_Yellow_Drive_Detected, Generator_Fusing_Detection. The processor 160 also ignores the results of any duty cycle calculation or power calculation. After stage 436, the method proceeds to stage 438. At stage 438, the processor 160 determines whether all bits are equal to 1. If all bits are equal to 1, the method proceeds to stage 440. If it is not the case that all bits are equal to 1, the method proceeds to stage 420.

Stages 440 and 420 both proceed to stage 442. Stage 442 starts a display portion of the method of FIG. 12B. At stage 442, the processor 160 determines whether test 3 was selected. If test 3 was selected, the method proceeds to stage 444. At stage 444, the processor 160 instructs handpiece test results to be displayed. The handpiece test results are displayed to the user. The results displayed to the user include only pass/fail results and do not include detailed values. After stage 444, the method proceeds to stage 452.

If at stage 442 it is determined that test 3 was not selected, the method proceeds to stage 446. At stage 446, the processor 160 determines whether test 2 was selected. If test 2 was selected, the method proceeds to stage 448. At stage 448, the processor 160 instructs generator and cable test results to be displayed. The generator and cable test results are displayed to the user. The results displayed to the user include only pass/fail results and do not include detailed values. After stage 444, the method proceeds to stage 452.

If at stage 442 it is determined that test 2 was not selected, the method proceeds to stage 450. At stage 450, the processor 160 instructs all test results to be displayed. The test results are displayed to the user. The test results include handpiece test results and generator and cable test results. The results displayed to the user include only pass/fail results and do not include detailed values.

After stage 450, 448, or 444, the method proceeds to stage 452. At stage 452, the processor 160 instructs the sending of the decoded test result and the displayed message to EMAIL@ADDRESS using the subject line "SUBJECT" followed by the code. The decoded test result comprises detailed values that were not displayed to the user. The displayed message is the message that was displayed to the user.

In other embodiments, any suitable system or function of the computing apparatus 150 or of a further computing apparatus or system may be provided with the decoded test results and/or with the displayed message, by any suitable communication means.

At stage 454, the processor 160 determines whether test 1 was passed. Test 1 is the full system test. If it is determined that test 1 has not been passed, the method proceeds to stage 458. At stage 458, the healthcheck code entry field is enabled to permit a repeat test to be performed. If at stage 454 it is determined that test 1 has been passed, the method proceeds to stage 456. At stage 456, the processor instructs the "Carry out healthcheck" option to be removed from the customer portal. Once the "Carry out healthcheck" option is removed, it is not possible for the customer to carry out a further healthcheck test unless the customer goes through a further booking procedure.

FIG. 15 shows tables listing tests with their corresponding website descriptions and calculation methods. FIG. 15 shows tests relating to the generator 101.

Column 700 lists tests as described above. Column 702 lists a website description that may be provided for each test. Column 704 shows the calculation result message displayed if the test is passed. If the test is passed, Logic 1 is recorded. In the present embodiment, PASS is displayed in each case when a test is passed. Column 706 shows the calculation result message displayed if the test is failed. If the test is failed, Logic 0 is recorded. In the present embodiment, FAIL is displayed in each case when a test is passed.

Column 708 shows comments on the messages displayed. A website description of GENERATOR TEST STATUS is displayed along with a pass or fail value for the generator as a whole. PASS is displayed if all of the tests are passed. FAIL is displayed if any of the tests are failed.

In some embodiments, only the overall generator test status pass or fail value is displayed to the user. In other embodiments, the pass and fail values for at least some of the individual tests are displayed to the user.

Column 710 shows calculations performed, which in this embodiment are the calculations of FIGS. 13 and 14. Columns 712 and 714 show low and high limits respectively. The calculated value for each parameter may be compared with a low limit and/or with a high limit for that parameter value. In the table of FIG. 15, numerical values for the limits are omitted for generality. Column 716 shows calculation notes.

A matrix 720 is used to determine a pass or fail for generator power in dependence on limits for both power and duty cycle. If duty cycle is high or very low, the test is failed. If duty cycle is typical and power is high, the test is failed. If duty cycle is typical and power is low or typical, the test is passed.

FIG. 16 shows tests relating to the cable 102.

Column 800 lists tests as described above. Column 802 lists a website description that may be provided for each test. Column 804 shows the calculation result message displayed if the test is passed. If the test is passed, Logic 1 is recorded. In the present embodiment, PASS is displayed in each case when a test is passed. Column 806 shows the calculation result message displayed if the test is failed. If the test is failed, Logic 0 is recorded. In the present embodiment, FAIL is displayed in each case when a test is passed.

Column 808 shows comments on the messages displayed. A website description of CABLE TEST STATUS is displayed along with a pass or fail value for the cable 102 as a whole. PASS is displayed if all of the tests are passed. FAIL is displayed if any of the tests are failed.

In some embodiments, only the overall cable test status pass or fail value is displayed to the user. In other embodiments, the pass and fail values for at least some of the individual tests are displayed to the user.

Column 810 shows calculations performed, which in this embodiment are the calculations of FIGS. 13 and 14. Columns 812 and 814 show low and high limits respectively. The calculated value for each parameter may be compared with a low limit and/or with a high limit for that parameter value. In the table of FIG. 16, numerical values for the limits are omitted for generality. Column 816 shows calculation notes.

A matrix 820 is used to determine a pass or fail for cable power in dependence on limits for both power and duty cycle. The matrix 820 for the cable power test differs from the matrix 720 for the generator power test.

If power is very low, the test is failed. If power is typical or high, the test is passed. The pass or fail value does not depend on duty cycle as the cable does not influence this parameter.

FIG. 17 shows tests relating to the handpiece 103.

Column 900 lists tests as described above. Column 902 lists a website description that may be provided for each test. Column 904 shows the calculation result message displayed if the test is passed. If the test is passed, Logic 1 is recorded. In the present embodiment, PASS is displayed in each case when a test is passed. Column 906 shows the calculation result message displayed if the test is failed. If the test is failed, Logic 0 is recorded. In the present embodiment, FAIL is displayed in each case when a test is passed. Column 908 shows comments on the messages displayed.

A website description of HANDPIECE TEST STATUS is displayed along with a pass or fail value for the handpiece 103 as a whole. PASS is displayed if all of the tests are passed. FAIL is displayed if any of the tests are failed.

In some embodiments, only the overall handpiece test status pass or fail value is displayed to the user. In other embodiments, the pass and fail values for at least some of the individual tests are displayed to the user.

Specific tests are described in embodiments above. In other embodiments, the portable test apparatus 110 may be configured to perform any suitable combination of tests. Results of the tests may be analysed within the portable test apparatus 110. Calculations may be performed within the portable test apparatus 110 based on test data obtained.

Test results may be output by the portable test apparatus to an external computing apparatus, for example via a website. Test results may be analysed externally. Calculations may be performed externally based on the test results.

Any suitable information may be provided to a user by the portable test apparatus 110 and/or by the external computing apparatus, for example via the website. Some information may be withheld from a user. For example, the user may be provided with pass/fail information rather than detailed test results.

Embodiments described above relate to the testing of a microwave treatment system outputting microwave energy. In other embodiments, a similar test apparatus and method may be used to test any RF treatment system outputting RF energy.

It may be understood that the present invention has been described above purely by way of example, and that modifications of detail can be made within the scope of the invention.

Each feature disclosed in the description and (where appropriate) the claims and drawings may be provided independently or in any appropriate combination.

The invention claimed is:

1. A portable test apparatus for testing an RF/microwave treatment system, the portable test apparatus comprising:
 a connector configured for connection to at least one of a generator or amplifier of the treatment system via a distal end of a reusable transmission cable of the treatment system;
 a measurement device configured for measuring RF/microwave energy received through the connector;
 a test controller configured to:
  run at least one test of a set of tests for testing the treatment system, at least some of the set of tests comprising using the measurement device to measure RF/microwave energy supplied by a generator or amplifier of the treatment system to a proximal end of the reusable transmission cable and transmitted through the reusable transmission cable to the connector; and
  at least one of analyse, record or output results of the set of tests; and
 a first transmission path configured to transmit RF/microwave energy from the connector to the measurement device, at least one further transmission path configured to transmit RF/microwave energy from the controller to at least one further RF/microwave component and a switch configured to switch between the first transmission path and the at least one further transmission path, wherein the switching of the switch is controlled by the test controller and wherein the test controller is configured to control the switch to switch between the first transmission path and the at least one further transmission path to perform different tests of the set of tests.

2. The apparatus according to claim 1, wherein the connector, measurement device and test controller are housed in a single housing.

3. The apparatus according to claim 1, wherein the test controller is configured to analyze the set of tests by performing at least one of a), b) or c):
 a) comparing the measured RF/microwave energy to predicted RF/microwave energy;
 b) comparing a measured value for a RF/microwave energy parameter to a threshold value for the RF/microwave energy parameter; or
 c) comparing a measured profile of the RF/microwave energy to an expected profile.

4. The apparatus according to claim 1, wherein the test controller is configured to analyze the set of tests to determine whether the reusable transmission cable is at least one of damaged or absorbing.

5. The apparatus according to claim 1, wherein the test controller is configured to analyze the set of tests by calculating a delivered power value using a measured power value and duty cycle value.

6. The apparatus according to claim 1, wherein the at least one RF/microwave component comprises at least one of a), b) or c):
 a) at least one reflecting component configured to reflect at least part of the RF/microwave energy back along the further transmission path through which it was transmitted to the at least one reflecting component;
 b) at least one RF/microwave load; or
 c) at least one of an open circuit or a short circuit.

7. The apparatus according to claim 6, wherein the set of tests comprises a reflected power trip test, wherein the reflected power trip test comprises determining by the test controller whether the generator or amplifier trips when RF/microwave energy is directed to the at least one reflecting component.

8. The apparatus according to claim 1, wherein the at least one RF/microwave component is configured to simulate at least one system condition, and wherein the test controller is configured to determine whether the generator or amplifier responded as expected to the simulated at least one system condition.

9. The apparatus according to claim 1, wherein at least one of a), b), c) or d):
 a) the at least one test of the set of tests comprises sending at least one signal from the portable test apparatus to the generator or amplifier, wherein the at least one test of the set of tests comprises verifying a response of the generator or amplifier to the at least one signal;
 b) the at least one test of the set of tests further comprises at least one data communication test, comprising testing data communication at least one of to or from the generator or amplifier;
 c) the set of tests is configured to test a plurality of parameters associated with the treatment system, the parameters including at least some of: continuity, voltage, current, resistance, electromagnetic energy, signal timing, identity, an audible alert, a visual alert, or a visible indicator; or
 d) the at least one test of the set of tests comprises measuring at least one of resistance properties or pulse/transient distance to fault timings to determine the integrity of at least one coaxial pathway.

10. The apparatus according to claim 1, further comprising a communication means configured to instruct the generator or amplifier to output energy in accordance with at least some of the set of tests.

11. The apparatus according to claim 1, further comprising a further connector configured to connect to an RF/microwave applicator device, wherein the at least one test of the set of tests further comprises at least one test for testing the RF/microwave applicator device, wherein the testing of the RF/microwave applicator device comprises testing at least one of: a functionality of the RF/microwave applicator device, an electrical property of the RF/microwave applicator device, an identity of the RF/microwave applicator device, a usage status of the RF/microwave applicator device, or communication to the RF/microwave applicator device.

12. The apparatus according to claim 1, further comprising a display configured to display a representation of at least one result of the set of tests, wherein the at least one result is encoded as at least one code word, wherein each code word is unique, and wherein the at least one code word comprises at least one of at least one binary word, at least one hexadecimal word or at least one multi-letter language word.

13. A test method for testing an RF/microwave treatment system using a portable test apparatus, the test method comprising:

connecting a generator or amplifier of the treatment system to a connector of the portable test apparatus by connecting a distal end of a reusable transmission cable of the treatment system to a connector of the portable test apparatus;

running, by a test controller of the portable test apparatus, at least one test of a set of tests for testing the treatment system, at least some of the set of tests comprising using the measurement device to measure RF/microwave energy supplied by a generator or amplifier of the treatment system to a proximal end of the reusable transmission cable and transmitted through the reusable transmission cable to the connector; and by the test controller, at least one of analyzing, recording or outputting results of the set of tests, wherein a first transmission path is configured to transmit RF/microwave energy from the connector to the measurement device, at least one further transmission path is configured to transmit RF/microwave energy from the controller to at least one further RF/microwave component and a switch is configured to switch between the first transmission path and the at least one further transmission path, wherein the switching of the switch is controlled by the test controller and wherein the test controller is configured to control the switch to switch between the first transmission path and the at least one further transmission path to perform different tests of the set of tests.

* * * * *